US012345417B2

(12) United States Patent
Liu et al.

(10) Patent No.: US 12,345,417 B2
(45) Date of Patent: Jul. 1, 2025

(54) HIGH TEMPERATURE CARBON MONOXIDE SENSOR FOR IN-SITU COMBUSTION MONITORING

(71) Applicant: West Virginia University Board of Governors on Behalf of West Virginia University, Morgantown, WV (US)

(72) Inventors: Xingbo Liu, Morgantown, WV (US); Yi Wang, Morgantown, WV (US); Liang Ma, Morgantown, WV (US); Wenyuan Li, Morgantown, WV (US)

(73) Assignee: THE WEST VIRGINIA UNIVERSITY BOARD OF GOVERNORS ON BEHALF OF WEST VIRGINIA UNIVERSITY, Morgantown, WV (US)

( * ) Notice: Subject to any disclaimer, the term of this patent is extended or adjusted under 35 U.S.C. 154(b) by 690 days.

(21) Appl. No.: 17/645,583

(22) Filed: Dec. 22, 2021

(65) Prior Publication Data
US 2022/0196239 A1    Jun. 23, 2022

Related U.S. Application Data

(60) Provisional application No. 63/199,401, filed on Dec. 23, 2020.

(51) Int. Cl.
| | |
|---|---|
| *F23N 5/00* | (2006.01) |
| *F23N 5/02* | (2006.01) |
| *G01N 27/30* | (2006.01) |
| *G01N 27/407* | (2006.01) |
| *G01N 33/00* | (2006.01) |

(52) U.S. Cl.
CPC ............. *F23N 5/006* (2013.01); *F23N 5/025* (2013.01); *G01N 27/30* (2013.01); *G01N 27/4073* (2013.01); *G01N 27/4075* (2013.01); *G01N 33/004* (2013.01); *F23N 2900/05004* (2013.01); *F23N 2900/05005* (2013.01)

(58) Field of Classification Search
CPC ..................... F23N 5/006; F23N 5/025; F23N 2900/05001; G01N 27/30; G01N 27/4073; G01N 27/4075; G01N 33/004; F01N 2560/022
See application file for complete search history.

(56) References Cited

FOREIGN PATENT DOCUMENTS

| EP | 18871 A | * | 11/1980 | ............. G01N 27/28 |
| EP | 0851226 A2 | * | 7/1998 | ........... G01N 27/407 |

OTHER PUBLICATIONS

EPO machine-generated English language translation of Croset et al. EP 18871 A, patent published Nov. 12, 1980 (Year: 1980).*

(Continued)

*Primary Examiner* — Alexander S Noguerola
(74) *Attorney, Agent, or Firm* — Buchanan Ingersoll & Rooney PC

(57) ABSTRACT

A high temperature carbon monoxide sensor for in-situ combustion monitoring is provided having a yttrium-stabilized zirconia interface based emf-measuring electrochemical sensor and a nickel oxide (NiO) first sensing electrode for targeting carbon monoxide gas at a temperature range from between about 1000 degrees Centigrade to about 1200 degrees Centigrade. A method of measuring carbon monoxide using this sensor is provided.

21 Claims, 19 Drawing Sheets

(56) References Cited

OTHER PUBLICATIONS

By Anggraini et al., "Stabilized zirconia-based planar sensor using coupled oxide(+Au) electrodes for highly selective CO detection," Sensors and Actuators B 160 (2011) 1273-1281 (Year: 2011).*

Wang et al., "A high-temperature mixed potential CO gas sensor for in situ combustion control," J. Mater. Chem. A, 2020, 8, 20101 (Year: 2020).*

Chong, Z. et al., Review of Natural Gas Hydrates as an Energy Resource: Prospects and Challenges, Applied Energy, 2015, pp. 1-20, Elsevier Ltd.

Ball, M. et al., The Future of Hydrogen—Opportunities and Challenges, International Journal of Hydrogen Energy 34, 2009, pp. 615-627, Elsevier Ltd.

Aguilera, R. et al., Revisiting the Role of Natural Gas as a Transition Fuel, Mineral Economics, 2019, pp. 1-8, Springer.

CO2 Emissions from Fuel Combustion, Database Documentation, 2019, pp. 1-73, International Energy Agency.

Docquier, N. et al., Combustion Control and Sensors: A Review, Progress in Energy and Combustion Science 28, 2002, pp. 107-150, Elsevier Science Ltd.

Sutton, J. et al., Digital, Interconnected Power Plants to Improve Efficiency and Reduce Emissions, Cornerstone, 2016, pp. 1-68, John Wiley & Sons, Inc.

Shuk, P. et al., Carbon Monoxide Gas Sensing Technologies in Combustion Process, Sensors & Transducers, 2017, pp. 1-13, IFSA Publishing.

Liu, F. et al., A Methodology to Constrain Carbon Dioxide Emissions from Coal-fired Power Plants Using Satellite Observations of Co-emitted Nitrogen Dioxide, Atoms. Chem. Phys., 2020, pp. 99-116, Copernicus Publications.

Kamas, J. et al., Predictive Emissions Monitoring Systems: A Low-Cost Alternative for Emissions Monitoring, 1995, pp. 497-509, IEEE-IAS.

Shuk, P. et al., Methane Gas Sensing Technologies in Combustion: Comprehensive Review, Sensors & Transducers, 2019, pp. 1-10, IFSA Publishing.

Zhang, L. et al., Programmed Fabrication of Metal Oxides Nanostructures Using Dual Templates to Spatially Disperse Metal Oxide Nanocrystals, Chem. Mater., 2010, 22, pp. 414-419, American Chemical Society.

Li, W. et al., Low-cost Synthesis of Graphitic Carbon Nanofibers as Excellent Room Temperature Sensors for Explosive Gases, J. Mater. Chem., 2012, 22, pp. 15342-15347, The Royal Society of Chemistry.

Lu, Y. et al., Preparation and Room Temperature Gas Sensing Study of Tungsten Oxide Nanowires/PEDOT/PSS Hybrid Materials, Ferroelectrics 477, 2015, pp. 93-102, Taylor & Francis Group, LLC.

Purbia, R. et al., Zero-dimensional Heterostructures: N-Doped Graphene Dots/SnO2 for Ultrasensitive and Selective NO2 Gas Sensing at Low Temperatures, J. Mater. Chem. A, 2020, pp. 1-9, The Royal Society of Chemistry.

Wang, D. et al., Catalytic-induced Sensing Effect of Triangular CeO2 Nanoflakes for Enhanced BTEX Vapor Detection with Conventional ZnO Gas Sensors, J. Mater. Chem. A, 2020, pp. 1-7, The Royal Society of Chemistry.

Zhang, X. et al., Layered Au, Pt-YSZ Mixed Potential Gas Sensing Electrode: Correlation Among Sensing Response, Dynamic Electrochemical Behavior and Structural Properties, Sensors and Actuators B: Chemical, 2018, pp. 1-22, Elsevier B.V.

Okamoto, H. et al., Carbon Monoxide Gas Sensor Made of Stabilized Zirconia, Solid State Ionics, 1980, pp. 319-326, North-Holland Publishing Company.

Ritter, T. et al., A Finite Element Model for Mixed Potential Sensors, Sensors and Actuators B: Chemical, 287, 2019, pp. 476-485, Elsevier B.V.

Miura, N. et al., A Review of Mixed-potential Type Zirconia-based Gas Sensors, Ionics, 2014, 20, pp. 901-925, Springer.

Anggraini, S. et al., YSZ-based Sensor Using Cr—Fe-based Spinel-oxide Electrodes for Selective Detection of CO, Analytica Chimica Acta, 2017, pp. 1-9, Elsevier B.V.

Mahendraprabhu, K. et al., CO Sensing Performances of YSZ-based Sensor Attached with Sol-gel Derived ZnO Nanospheres, Sensors and Actuators B: Chemical, 2018, pp. 1-25, Elsevier B.V.

Tho, N. et al., High Temperature Calcination for Analyzing Influence of 3d Transition Metals on Gas Sensing Performance of Mixed Potential Sensor Pt/YSZ/LaMO3 (M = Mn, Fe, Co, Ni), Electrochimica Acta, 190, 2016, pp. 215-220, Elsevier Ltd.

Yamaguchi, M. et al., Selective Hydrogen Detection at High Temperature by Using Yttria-stabilized Zirconia-based Sensor with Coupled Metal-oxide-based Sensing Electrodes, Electrochimica Acta, 76, 2012, pp. 152-158, Elsevier Ltd.

Lau, J. et al., Thermodynamic Assessment of CO2 to Carbon Nanofiber Transformation for Carbon Sequestration in a Combined Cycle Gas or a Coal Power Plant, Energy Conversion and Management, 122, 2016. pp. 400-410, Elsevier Ltd.

Chase, M., NIST-JANAF Thermochemical Tables Fourth Edition Part I, Al—Co, J. Phys. Chem. Ref. Data, 1998, pp. 1-61, American Chemical Society.

* cited by examiner

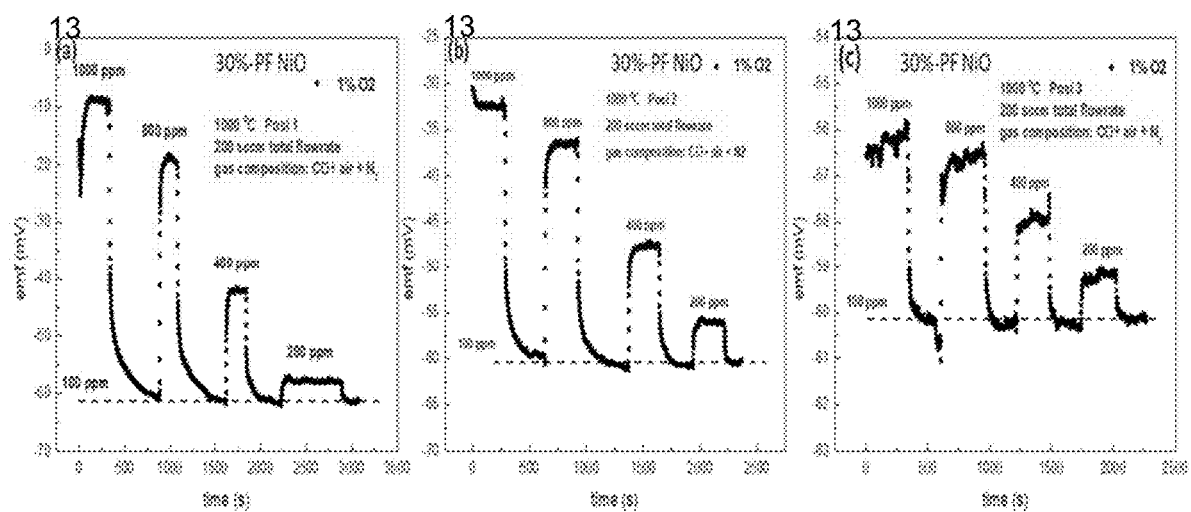
Fig. 13(a), Fig. 13(b), and Fig. 13(c)

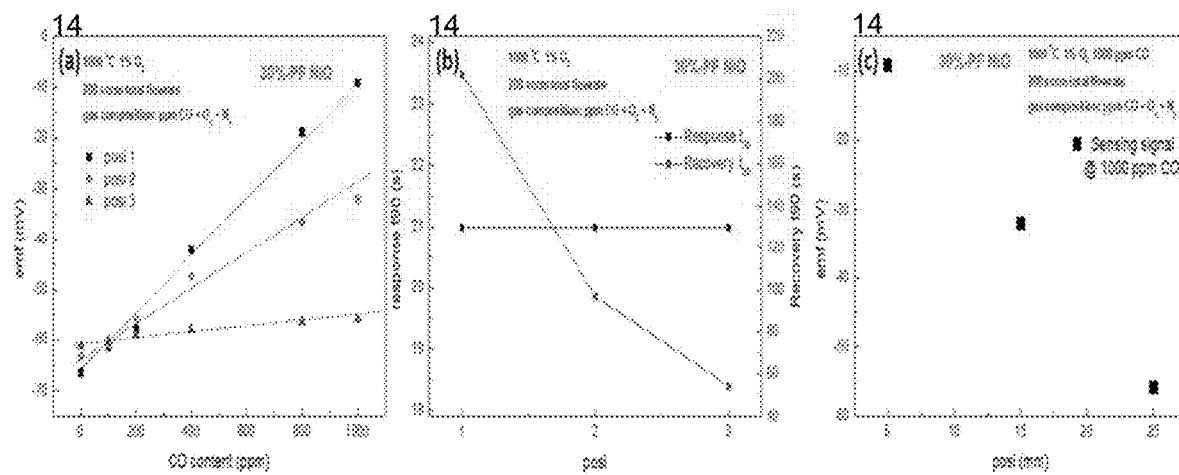
Fig. 14(a), Fig. 14(b), and Fig. 14(c)

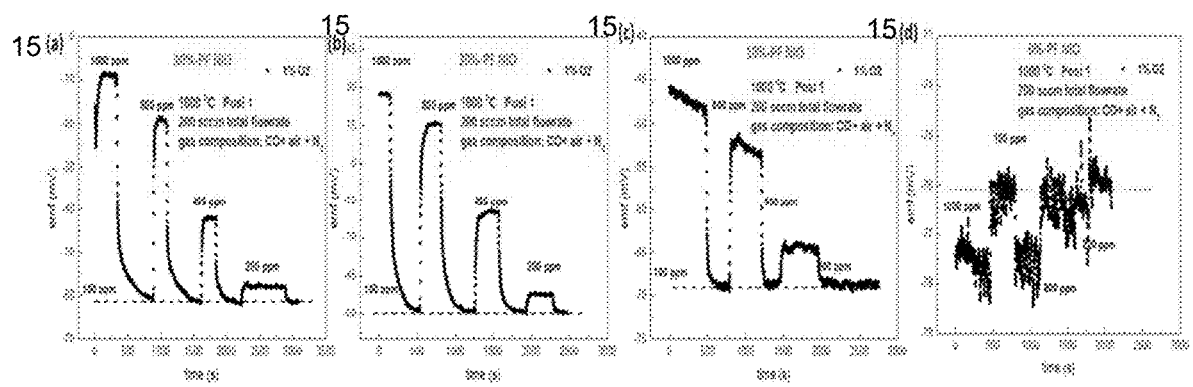
Fig. 15(a), Fig. 15(b), Fig. 15(c), and Fig. 15(d)

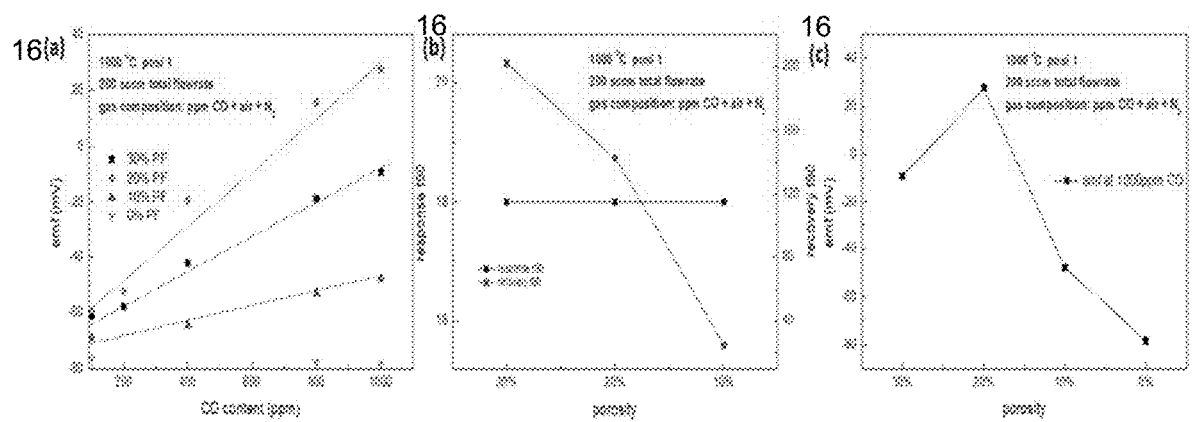
Fig. 16(a), Fig. 16(b), and Fig. 16(c)

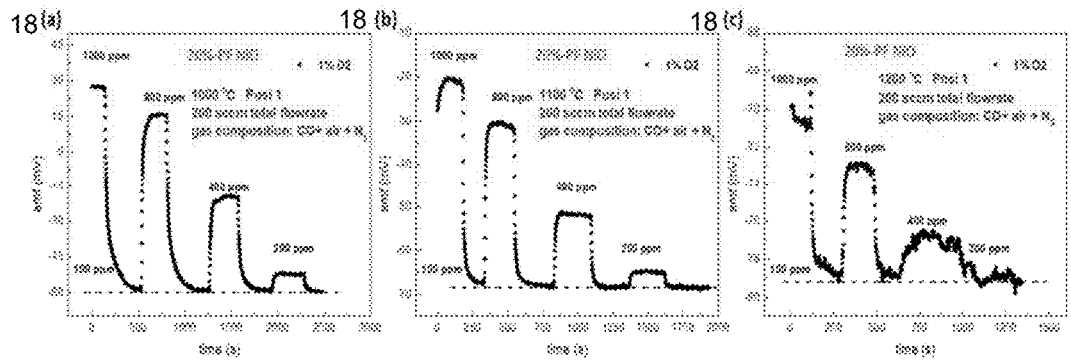
Fig. 18(a), Fig. 18 (b), and Fig. 18(c)
- 95 mV signal to 1000 ppm CO @1000 C + 1%$O_2$,
- C40 mV signal to 1000 ppm CO @1100C +1%$O_2$,
- 5 mV signal to 1000 ppm CO @ 1200 C+ 1% $O_2$
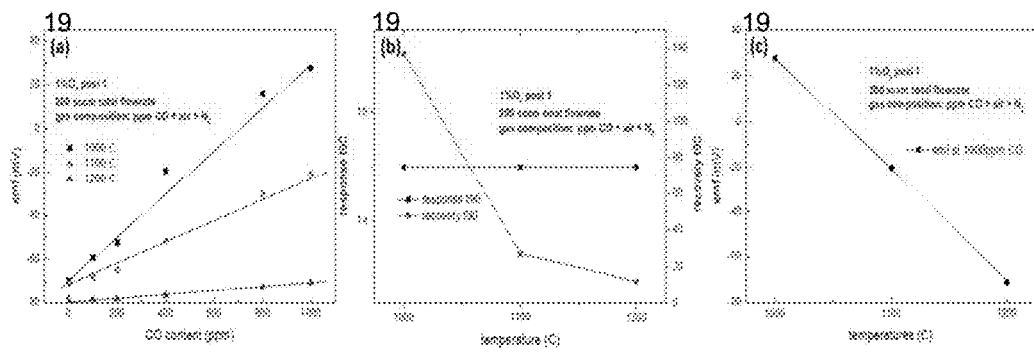
Fig. 19(a), Fig. 19(b), and Fig. 19(c)

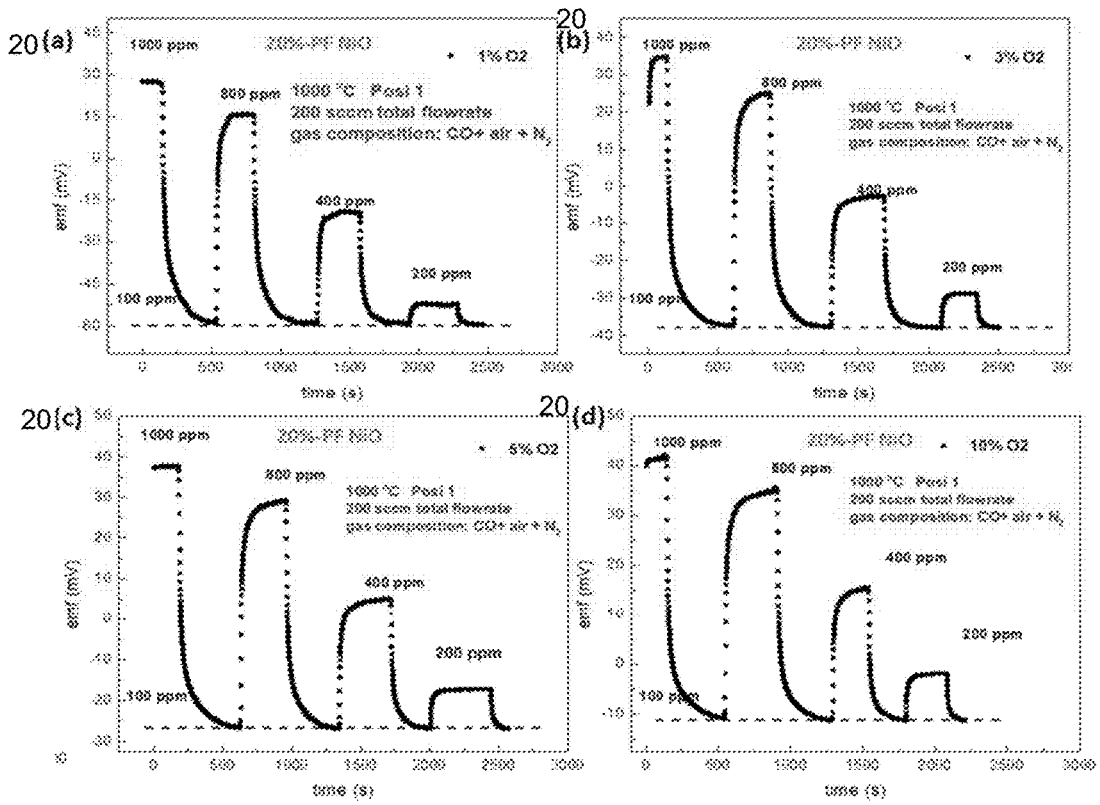
- 95 mV signal to 1000 ppm CO @1000 C + 1%$O_2$,
- 80 mV signal to 1000 ppm CO @1000C +3%$O_2$,
- 60 mV signal to 1000 ppm CO @ 1000 C+ 5% $O_2$
- 50 mV signal to 1000 ppm CO @ 1000 C+ 10% $O_2$
Fig. 20(a), Fig. 20(b), Fig. 20(c), and Fig. 20(d)

HIGH TEMPERATURE CARBON MONOXIDE SENSOR FOR IN-SITU COMBUSTION MONITORING

CROSS-REFERENCE TO RELATED APPLICATION

This utility non-provisional patent application claims the benefit of priority to U.S. Provisional Patent Application Ser. No. 63/199,401, filed Dec. 23, 2020. The entire contents of U.S. Provisional Patent Application Ser. No. 63/199,401 is incorporated by reference into this utility non-provisional patent application as if fully rewritten herein.

STATEMENT REGARDING FEDERALLY SPONSORED RESEARCH OR DEVELOPMENT

This invention was made with government support under Grant No. DE-FE0031564 awarded by the Department of Energy. The government has certain rights in the invention.

BACKGROUND OF THE INVENTION

1. Field of the Invention

The present invention relates to a high temperature carbon monoxide sensor for in-situ combustion monitoring. More preferably, this invention provides a high temperature carbon monoxide sensor for in-situ combustion monitoring in a coal-based power plant. In certain embodiments of this invention, a high temperature carbon monoxide sensor comprising a yttrium-stabilized zirconia interface based emf-measuring electrochemical sensor and a nickel oxide (NiO) first sensing electrode for targeting carbon monoxide gas at a temperature range from between about 1000 degrees Centigrade to about 1200 degrees Centigrade is provided.

2. Description of the Background Art

Carbon Monoxide (CO) concentration is one of the most important parameters for controlling combustion kinetics to achieve high efficiency and low emissions in fossil fueled engines and power plants (boilers and gas turbines). Currently, mixed potential CO sensors have been developed and deployed in internal combustion (IC) engines where the temperature is below 700 C. No cost-effective and reliable in-situ CO sensor is available for high temperature (1000 degrees Centigrade or above) combustion, in boilers and gas turbines.

Currently, continuous emissions monitoring systems (CEMS) use a pollutant analyzer, algebra conversion equations, or a computer program to evaluate the gas or particulate specifies offers strong benefits to the power plant operation. However, these current known systems are expensive and require 1) the extraction of flue gas from the boiler, 2) the use of gas filters or traps, and 3) trained personnel to correctly handle the monitoring, which add a delay between the measurement and the real-time dynamic combustion. Calorimetric analyzers using resistivity temperature detectors to detect the heat of oxidation from a catalyst layer have only been demonstrated as an extractive approach, which is not especially suitable for real-time boiler control. Optical sensing approaches, e.g. tunable diode or quantum cascade laser spectroscopies are still not reliable enough given that a large amount of substances impede light transmission and the measured value is not local but an average one among the light path. Chemical resistive sensors based on semiconducting oxides are used widely for various gas sensing at relatively lower temperature (<300 degrees C.). However, the lack of selectivity to some combustible gases and insufficient long-term stability at extremely high temperature may be the problem.

SUMMARY OF THE INVENTION

The present invention provides a high temperature carbon monoxide sensor for in-situ combustion monitoring.

In certain embodiments of this invention, a high temperature carbon monoxide sensor comprising a yttrium-stabilized zirconia interface based emf-measuring electrochemical sensor and a nickel oxide (NiO) first sensing electrode for targeting carbon monoxide gas at a temperature range from between about 1000 degrees Centigrade to about 1200 degrees Centigrade. In certain embodiments of this invention, the high temperature carbon monoxide sensor includes a platinum second sensing electrode for targeting oxygen gas. In another embodiment of this invention, the high temperature carbon monoxide sensor includes wherein the yttrium-stabilized zirconia is in the form of a solid electrolyte.

In certain embodiments of this invention, a high temperature carbon monoxide sensor is provided comprising (i) a housing having a first end and a second end and a middle section disposed between said first end of said housing and said second end of said housing, said housing having an external wall and an internal wall; (ii) a chamber having an internal wall and an external wall, and wherein said chamber having a first open end and a second open end and wherein the second open end of said chamber is opposite to said first open end of said chamber, and wherein said external wall of said chamber is surrounded at least in part by said internal wall of said housing; (iii) a first alumina tube having an external wall and an internal wall, said first alumina tube has a first open end and a second open end, and a middle section disposed between said first open end and said second open end of said first alumina tube, wherein at least a portion of said first alumina tube is located within said chamber; (iv) a thermocouple wherein at least a portion of said thermocouple is located within said chamber; (v) a sensor probe wherein said sensor probe is located within and is in sealed engagement with said second open end of said first alumina tube wherein said sensor probe comprises a first sensing electrode and a reference electrode, and a yttrium-stabilized zirconia interface, and optionally a second sensing electrode, wherein said yttrium-stabilized zirconia interface is disposed between (a) said first sensing electrode and (b) said reference electrode, or optionally wherein said yttrium-stabilized zirconia interface is disposed between (a) said first sensing electrode and said second sensing electrode and (b) said reference electrode; (v) a porous ceramic element, wherein said porous ceramic element is located within said second open end of said chamber; and (vi) wherein said first sensing electrode is in communication with a first sensing electrode wire, wherein said second sensing electrode is in communication with a second sensing electrode wire, wherein said reference electrode is in communication with a reference electrode wire, and wherein a thermocouple wire is in communication with said thermocouple, and wherein at least a portion of each of said first sensing electrode wire, said second sensing electrode wire, said thermocouple wire, and said reference electrode wire are located in an interior of said middle section of said first alumina tube.

In certain embodiments of the high temperature carbon monoxide sensor of this invention, an insulating layer is provided wherein the insulating layer is in juxtaposition to at least a portion of the internal wall of the housing and at least a portion of the external wall of the chamber.

In another embodiment of this invention, the high temperature carbon monoxide sensor includes wherein each of said first sensing electrode wire, said second sensing electrode wire, said thermocouple wire, and said reference electrode wire are made of a heat-resistant material.

In certain embodiments of this invention the first sensing electrode is a nickel oxide sensing electrode, the second sensing electrode is a platinum sensing electrode, and the reference electrode is a platinum reference electrode.

Another embodiment of this invention provides a high temperature carbon monoxide sensor system comprising (A) a high temperature carbon monoxide sensor comprising (i) a housing having a first end and a second end and a middle section disposed between said first end of said housing and said second end of said housing, said housing having an external wall and an internal wall; (ii) a chamber having an internal wall and an external wall, and wherein said chamber having a first open end and a second open end and wherein the second open end of said chamber is opposite to said first open end of said chamber, and wherein said external wall of said chamber is surrounded at least in part by said internal wall of said housing; (iii) a first alumina tube having an external wall and an internal wall, said first alumina tube has a first open end and a second open end, and a middle section disposed between said first open end and said second open end of said first alumina tube, wherein at least a portion of said first alumina tube is located within said chamber; (iv) a thermocouple wherein at least a portion of said thermocouple is located within said chamber; (v) a sensor probe wherein said sensor probe is located within and is in sealed engagement with said second open end of said first alumina tube wherein said sensor probe comprises a first sensing electrode and a reference electrode, and a yttrium-stabilized zirconia interface, and optionally a second sensing electrode, wherein said yttrium-stabilized zirconia interface is disposed between (a) said first sensing electrode and (b) said reference electrode, or optionally wherein said yttrium-stabilized zirconia interface is disposed between (a) said first sensing electrode and said second sensing electrode and (b) said reference electrode; (v) a porous ceramic element, wherein said porous ceramic element is located within said second open end of said chamber; and (vi) wherein said first sensing electrode is in communication with a first sensing electrode wire, wherein said second sensing electrode is in communication with a second sensing electrode wire, wherein said reference electrode is in communication with a reference electrode wire, and wherein a thermocouple wire is in communication with said thermocouple, and wherein at least a portion of each of said first sensing electrode wire, said second sensing electrode wire, said thermocouple wire, and said reference electrode wire are located in an interior of said middle section of said first alumina tube; and (B) a data collector system comprising a first voltmeter, a second voltmeter, and a thermometer, and wherein said first sensing electrode is in communication with said first voltmeter via a first sensing electrode wire, wherein said second sensing electrode is in communication with said second voltmeter via said second sensing electrode wire, wherein said reference electrode is in communication with said first voltmeter and said second voltmeter via a reference electrode wire, and wherein a thermocouple wire is in communication with said thermocouple and said thermometer, and wherein a portion of each of said first sensing electrode wire, said second sensing electrode wire, and said thermocouple wire are located in an interior of said middle section of said first alumina tube.

In another embodiment of this invention, a high temperature carbon monoxide sensor is provided comprising a yttrium-stabilized zirconia interface based emf-measuring electrochemical sensor and a first sensing electrode for targeting carbon monoxide gas at a temperature range from between about 1000 degrees Centigrade to about 1200 degrees Centigrade. In certain embodiments of this invention, the high temperature carbon monoxide sensor includes a second sensing electrode. The high temperature carbon monoxide sensor may include wherein the yttrium-stabilized zirconia interface is in the form of a solid electrolyte. The first sensing electrode, and the optional second sensing electrode, may be each independently made of a material that is one independently selected from the group consisting essentially of (i) NiO, (ii) NiO doped with the following doping material $ZrO_2$ and doping element stabilized zirconia such as Yttria stabilized Zirconia (YSZ), Samaria Stabilized Zirconia (SSZ), and Calcium stabilized Zirconia (CSZ), (iii) NiO doped with ceria, (iv) NiO doped with ceria that is one selected from the group consisting essentially of Gadolinium doped Ceria (GDC) and Samarium doped Ceria (SDC); (v) NiO doped with CuO, (vi) NiO doped with FeO, (vii) NiO doped with $Al_2O_3$, (viii) NiO doped with infiltrated spinel, (ix) NiO doped with NiFe spinel, (x) NiO doped with NiAl spinel, and (xi) NiO doped with platinum.

In another embodiment of this invention, a method of measuring carbon monoxide in a combustion process environment comprising using a high temperature carbon monoxide sensor system comprising a high temperature carbon monoxide sensor comprising a yttrium-stabilized zirconia interface based emf-measuring electrochemical sensor and a nickel oxide (NiO) first sensing electrode for targeting carbon monoxide gas at a temperature range from between about 1000 degrees Centigrade to about 1200 degrees Centigrade. In certain embodiments of the method of this invention, the combustion process environment is that of a power plant. In certain other embodiments of this method of measuring carbon monoxide, includes wherein the high temperature carbon monoxide sensor includes a platinum second sensing electrode for targeting oxygen gas. In certain embodiments of the method of this invention, the yttrium-stabilized zirconia is in the form of a solid electrolyte.

Another embodiment of this invention provides a method of measuring carbon monoxide in a combustion process environment comprising using a high temperature carbon monoxide sensor system comprising (A) a high temperature carbon monoxide sensor comprising (i) a housing having a first end and a second end and a middle section disposed between said first end of said housing and said second end of said housing, said housing having an external wall and an internal wall; (ii) a chamber having an internal wall and an external wall, and wherein said chamber having a first open end and a second open end and wherein the second open end of said chamber is opposite to said first open end of said chamber, and wherein said external wall of said chamber is surrounded at least in part by said internal wall of said housing; (iii) a first alumina tube having an external wall and an internal wall, said first alumina tube has a first open end and a second open end, and a middle section disposed between said first open end and said second open end of said first alumina tube, wherein at least a portion of said first alumina tube is located within said chamber; (iv) a thermocouple wherein at least a portion of said thermocouple is located within said chamber; (v) a sensor probe wherein said sensor probe is located within and is in sealed engagement with said second open end of said first alumina tube wherein said sensor probe comprises a first sensing electrode and a reference electrode, and a yttrium-stabilized zirconia interface, and optionally a second sensing electrode, wherein said yttrium-stabilized zirconia interface is disposed between (a) said first sensing electrode and (b) said reference electrode, or optionally wherein said yttrium-stabilized zirconia interface is disposed between (a) said first sensing electrode and said second sensing electrode and (b) said reference electrode; (v) a porous ceramic element, wherein said porous ceramic element is located within said second open end of said chamber; and (vi) wherein said first sensing electrode is in communication with a first sensing electrode wire, wherein said second sensing electrode is in communication with a second sensing electrode wire, wherein said reference electrode is in communication with a reference electrode wire, and wherein a thermocouple wire is in communication with said thermocouple, and wherein at least a portion of each of said first sensing electrode wire, said second sensing electrode wire, said thermocouple wire, and said reference electrode wire are located in an interior of said middle section of said first alumina tube; and (B) a data collector system comprising a first voltmeter, a second voltmeter, and a thermometer, and wherein said first sensing electrode is in communication with said first voltmeter via a first sensing electrode wire, wherein said second sensing electrode is in communication with said second voltmeter via said second sensing electrode wire, wherein said reference electrode is in communication with said first voltmeter and said second voltmeter via a reference electrode wire, and wherein a thermocouple wire is in communication with said thermocouple and said thermometer, and wherein a portion of each of said first sensing electrode wire, said second sensing electrode wire, and said thermocouple wire are located in an interior of said middle section of said first alumina tube. In certain embodiments of this method of measuring carbon monoxide in a combustion process environment includes wherein the first sensing electrode is a nickel oxide sensing electrode, the second sensing electrode is a platinum sensing electrode, and the reference electrode is a platinum reference electrode.

BRIEF DESCRIPTION OF THE DRAWINGS

Figure 7:
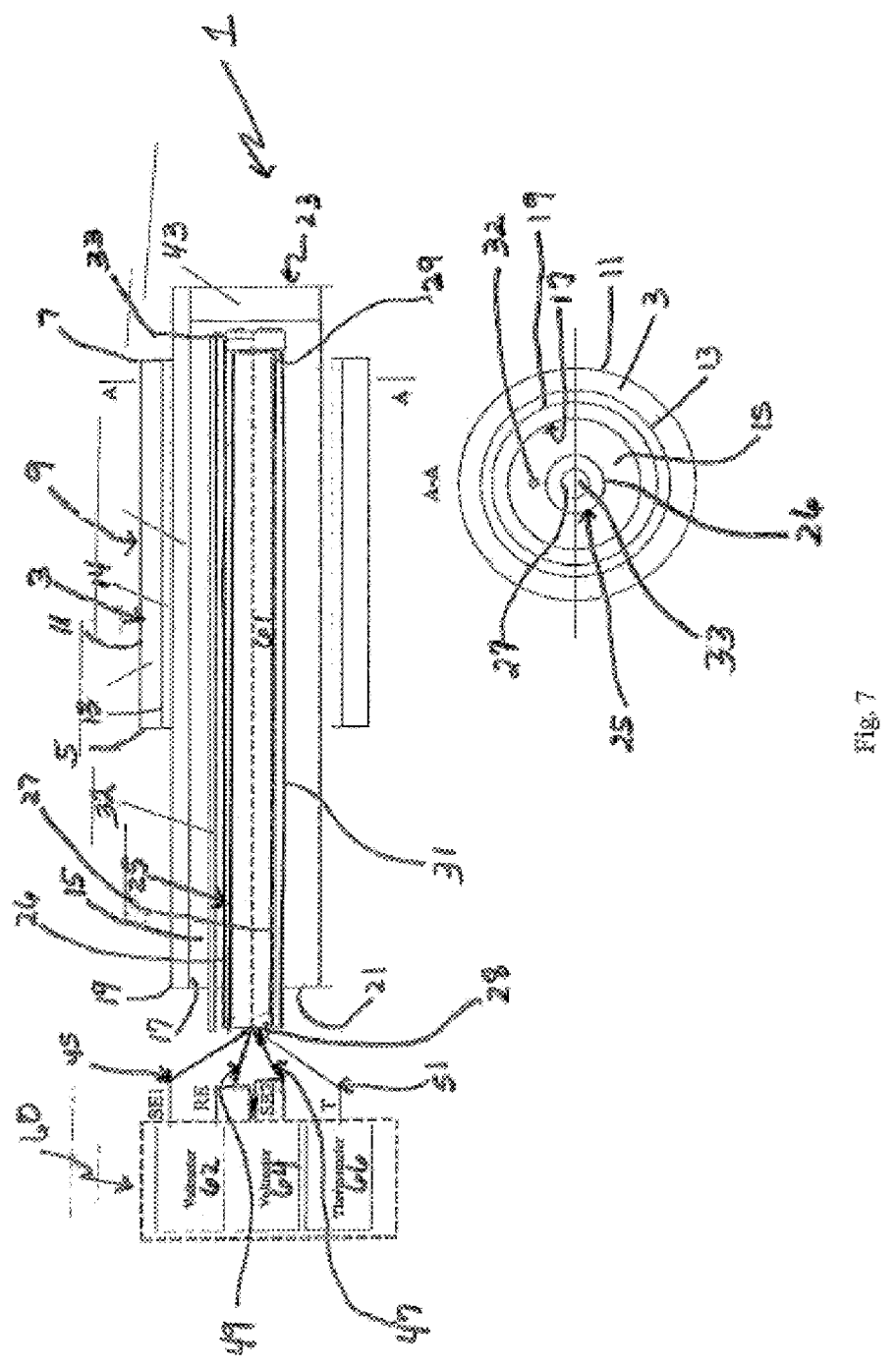

FIG. 7 shows one embodiment the structure of the high temperature carbon monoxide gas sensor (1) of this invention.

FIG. 13(a) shows emf sensing signal of 30%-PF NiO to CO under 1% $O_2$ and 1000° C.

FIG. 13(b) shows emf sensing signal of 30%-PF NiO to CO under 1% $O_2$ and 1000° C.

FIG. 13(c) shows emf sensing signal of 30%-PF NiO to CO under 1% $O_2$ and 1000° C.

FIG. 14(a) shows results of sensing signal.

FIG. 14(b) shows results of response $t_{90}$ (top and bottom vertical lines) and recovery $t_{90}$ (horizontal line).

FIG. 14(c) shows results of 1000 ppm signal vs inlet tube position.

FIG. 15(a) shows sensing behavior of NiO to CO under 1% $O_2$ and 1000° C. vs. varied porosities of NiO SE.

FIG. 15(b) shows sensing behavior of NiO to CO under 1% $O_2$ and 1000° C. vs. varied porosities of NiO SE.

FIG. 15(c) shows sensing behavior of NiO to CO under 1% $O_2$ and 1000° C. vs. varied porosities of NiO SE.

FIG. 15(d) shows sensing behavior of NiO to CO under 1% $O_2$ and 1000° C. vs. varied porosities of NiO SE.

FIG. 16(a) shows results of sensing signal.

FIG. 16(b) shows results of response $t_{90}$ (horizontal line) and recovery $t_{90}$ (top and bottom vertical lines).

FIG. 16(c) shows results of 1000 ppm signal vs inlet SE porosities.

FIG. 18(a) shows sensing behavior of 30% PF NiO to CO under 1% $O_2$ vs. varied working temperatures.

FIG. 18(b) shows sensing behavior of 30% PF NiO to CO under 1% $O_2$ vs. varied working temperatures.

FIG. 18(c) shows sensing behavior of 30% PF NiO to CO under 1% $O_2$ vs. varied working temperatures.

FIG. 19(a) shows results of sensing signal.

FIG. 19(b) shows results of response $t_{90}$ (horizontal line) and recovery $t_{90}$ (top and bottom vertical lines).

FIG. 19(c) shows results of 1000 ppm signal vs different temperatures.

FIG. 20(a) shows sensing behavior of 30% PF NiO to CO under 1000° C. vs. varied oxygen content.

FIG. 20(b) shows sensing behavior of 30% PF NiO to CO under 1000° C. vs. varied oxygen content.

FIG. 20(c) shows sensing behavior of 30% PF NiO to CO under 1000° C. vs. varied oxygen content.

FIG. 20(d) shows sensing behavior of 30% PF NiO to CO under 1000° C. vs. varied oxygen content.

DETAILED DESCRIPTION OF THE INVENTION

Figure 1:
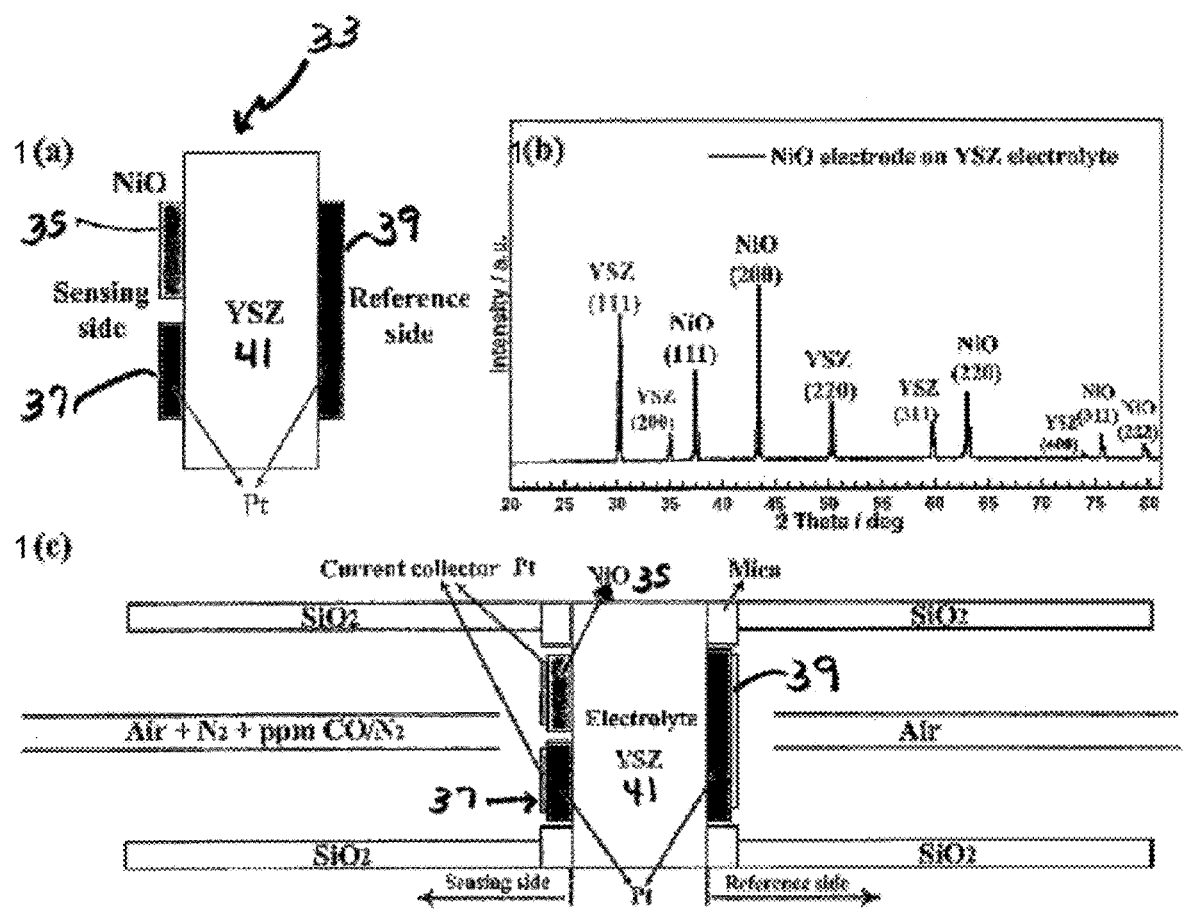
FIG. 1(a) shows (a) structure of the YSZ-based mixed potential sensor consisting of YSZ electrolyte, NiO sensing electrode, Pt sensing electrode and reference electrode.
FIG. 1(b) shows XRD of the porous NiO electrode for as-prepared sensor sample.
FIG. 1(c) shows lab test configuration for the CO testing for all lab-test results presented herein.

A high temperature CO sensor was developed that can operate at 1000 degrees centigrade (C) or above, which can allow the in-situ monitoring of combustion. The operators can use it to adjust operation, such as air to fuel ratio, to achieve high efficiency and low emissions.

The current method for monitoring the air to fuel ratio in fossil fuel power plants involves extracting flue gas, cooling it, and laboratory testing it using gas chromatography. The process takes about 30 minutes and the results do not reflect what is actually happening in the plant's boiler at the moment combustion is occurring. This sensor allows real-time monitoring so that power plants can operate at optimal efficiency in real time, which translates into the potential for increased revenue and decreased fuel costs. For example, at the power plant where the sensor of this invention was tested, a one percent increase in efficiency translates into approximately $20,000 in additional revenue per day. Maintaining the optimal air to fuel ratio also reduces emissions, especially with regard to nitrogen oxides that contribute to smog. Further, as more renewables come online and states mandate renewables are dispatched first, fossil fuel plants will need to track electricity demand, known as load following. Load following generally occurs over the course of a few seconds, not on the order of 30 minutes. Nickel oxide (NiO) is the critical sensing material. Sensor design, such as geometry, morphology, and microstructure of each electrode are also important.

In one embodiment of this invention a high temperature carbon monoxide sensor for in-situ combustion monitoring is provided that is a mixed potential, CO (carbon monoxide), high temperature (>=1000 degrees Centigrade (C)) sensor.

In an embodiment of this invention a high temperature carbon monoxide sensor for in-situ combustion monitoring is provided.

As used herein, the term "high temperature" refers to a temperature of from greater than or equal to about 1000 degrees Centigrade.

As used herein, the term "dense NiO" means that the fabricated NiO electrode has a density>90% and that there are no obvious holes in the cross-section microscopy image.

As used herein, the term "porous NiO" means that the fabricated NiO electrode has a density<65% and that there are obvious holes in the cross-section microscopy image.

The present invention is set forth in at least FIG. 1(a), FIG. 7, FIG. 9(a), FIG. 10, and FIG. 12(a), of a high temperature carbon monoxide sensor (1) comprising a yttrium-stabilized zirconia interface based emf-measuring electrochemical sensor (41) and a nickel oxide (NiO) first sensing electrode (35) for targeting carbon monoxide gas at a temperature range from between about 1000 degrees Centigrade to about 1200 degrees Centigrade. In certain embodiments of this invention, the high temperature carbon monoxide sensor (1) includes a platinum second sensing electrode (37) for targeting oxygen gas. The high temperature carbon monoxide sensor (1) may include wherein the yttrium-stabilized zirconia interface (41) is in the form of a solid electrolyte.

In another embodiment of this invention, as set forth in at least FIG. 1(a), FIG. 7, FIG. 9(a), FIG. 10, and FIG. 12(a), a high temperature carbon monoxide sensor (1) is provided comprising a yttrium-stabilized zirconia interface based emf-measuring electrochemical sensor (41) and a first sensing electrode (35) for targeting carbon monoxide gas at a temperature range from between about 1000 degrees Centigrade to about 1200 degrees Centigrade. In certain embodiments of this invention, the high temperature carbon monoxide sensor (1) includes a second sensing electrode (37). The high temperature carbon monoxide sensor (1) may include wherein the yttrium-stabilized zirconia interface (41) is in the form of a solid electrolyte. The first sensing electrode, and the optional second sensing electrode, may be each independently made of a material that is one independently selected from the group consisting essentially of (i) NiO, (ii) NiO doped with the following doping material ZrO2 and doping element stabilized zirconia such as Yttria stabilized Zirconia (YSZ), Samaria Stabilized Zirconia (SSZ), and Calcium stabilized Zirconia (CSZ), (iii) NiO doped with ceria, (iv) NiO doped with ceria that is one selected from the group consisting essentially of Gadolinium doped Ceria (GDC) and Samarium doped Ceria (SDC); (v) NiO doped with CuO, (vi) NiO doped with FeO, (vii) NiO doped with $Al_2O_3$, (viii) NiO doped with infiltrated spinel, (ix) NiO doped with NiFe spinel, (x) NiO doped with NiAl spinel, and (xi) NiO doped with platinum. The present inventors have unexpectedly found that the use of a first sensing electrode and/or a second sensing electrode that is/are made of a composite material(s) as set forth above increases the first sensing electrode's and/or the second sensing electrode's structure and thermal stability with minimal compromise to the first sensing electrode's and/or the second sensing electrode's sensitivity.

In a certain embodiment of the present invention, a high temperature carbon monoxide sensor for in-situ combustion monitoring is provided. As set forth in at least FIG. 1(a), FIG. 7, FIG. 9(a), FIG. 10, and FIG. 12(a), the high temperature carbon monoxide sensor (1) comprises: (i) a housing (3) having a first end (5) and a second end (7) and a middle section (9) disposed between said first end (5) of said housing (3) and said second end (7) of said housing (3), said housing (3) having an external wall (11) and an internal wall (13); (ii) a chamber (15) having an internal wall (17) and an external wall (19), and wherein said chamber (15) having a first open end (21) and a second open end (23) and wherein the second open end (23) of said chamber (15) is opposite to said first open end (21) of said chamber (15), and wherein said external wall (19) of said chamber (15) is surrounded at least in part by said internal wall (13) of said housing (3); (iii) a first alumina tube (25) having an external wall (26) and an internal wall (27), said first alumina tube (25) has a first open end (28) and a second open end (29), and a middle section (31) disposed between said first open end (28) and said second open end (29) of said first alumina tube (25), wherein at least a portion of said first alumina tube (25) is located within said chamber (15); (iv) a thermocouple (32) wherein at least a portion of said thermocouple (32) is located within said chamber (15); (v) a sensor probe (33) wherein said sensor probe is located within and is in sealed engagement with said second open end (29) of said first alumina tube (25) wherein said sensor probe (33) comprises a first sensing electrode (35) and a reference electrode (39), and a yttrium-stabilized zirconia interface ("YSZ") (41), and optionally a second sensing electrode (37), wherein said yttrium-stabilized zirconia interface (41) is disposed between (a) said first sensing electrode (35) and (b) said reference electrode (39), or optionally wherein said yttrium-stabilized zirconia interface (41) is disposed between (a) said first sensing electrode (35) and said second sensing electrode (37) and (b) said reference electrode (39); (v) a porous ceramic element (43) (for example but not limited to a refractory brick, a ceramic porous brick, or a porous ceramic layer), wherein said porous ceramic element (43) is located within said second open end (23) of said chamber (15); and (vi) wherein said first sensing electrode (35) is in communication with a first sensing electrode wire (45), wherein said second sensing electrode (37) is in communication with a second sensing electrode wire (47), wherein said reference electrode (39) is in communication with a reference electrode wire (49), and wherein a thermocouple wire (51) is in communication with said thermocouple (32), and wherein at least a portion of each of said first sensing electrode wire (45), said second sensing electrode wire (47), said thermocouple wire (51), and said reference electrode wire (49) are located in an interior (61) of said middle section (31) of said first alumina tube (25). The high temperature carbon monoxide sensor (1) described above optionally includes an insulating layer (14) (such as for example but not limited to asbestos, a ceramic layer, or a refractory material) wherein the insulating layer (14) is in juxtaposition to at least a portion of the internal wall (13) of said housing (3) and at least a portion of said external wall (19) of said chamber (15).

In another embodiment of this invention, the high temperature carbon monoxide sensor (1) includes wherein each of said first sensing electrode wire (45), said second sensing electrode wire (47), said thermocouple wire (51), and said reference electrode wire (49) are made of a heat-resistant material.

Another embodiment of this invention provides a high temperature carbon monoxide sensor system comprising: (A) high temperature carbon monoxide sensor (1) comprises: (i) a housing (3) having a first end (5) and a second end (7) and a middle section (9) disposed between said first end (5) of said housing (3) and said second end (7) of said housing (3), said housing (3) having an external wall (11) and an internal wall (13); (ii) a chamber (15) having an internal wall (17) and an external wall (19), and wherein said chamber (15) having a first open end (21) and a second open end (23) and wherein the second open end (23) of said chamber (15) is opposite to said first open end (21) of said chamber (15), and wherein said external wall (19) of said chamber (15) is surrounded at least in part by said internal wall (13) of said housing (3); (iii) a first alumina tube (25) having an external wall (26) and an internal wall (27), said first alumina tube (25) has a first open end (28) and a second open end (29), and a middle section (31) disposed between said first open end (28) and said second open end (29) of said first alumina tube (25), wherein at least a portion of said first alumina tube (25) is located within said chamber (15); (iv) a thermocouple (32) wherein at least a portion of said thermocouple (32) is located within said chamber (15); (v) a sensor probe (33) wherein said sensor probe is located within and is in sealed engagement with said second open end (29) of said first alumina tube (25) wherein said sensor probe (33) comprises a first sensing electrode (35) and a reference electrode (39), and a yttrium-stabilized zirconia interface ("YSZ") (41), and optionally a second sensing electrode (37), wherein said yttrium-stabilized zirconia interface (41) is disposed between (a) said first sensing electrode (35) and (b) said reference electrode (39), or optionally wherein said yttrium-stabilized zirconia interface (41) is disposed between (a) said first sensing electrode (35) and said second sensing electrode (37) and (b) said reference electrode (39); (v) a porous ceramic element (43) (for example but not limited to a refractory brick, a ceramic porous brick, or a porous ceramic layer), wherein said porous ceramic element (43) is located within said second open end (23) of said chamber (15); and (vi) wherein said first sensing electrode (35) is in communication with a first sensing electrode wire (45), wherein said second sensing electrode (37) is in communication with a second sensing electrode wire (47), wherein said reference electrode (39) is in communication with a reference electrode wire (49), and wherein a thermocouple wire (51) is in communication with said thermocouple (32), and wherein at least a portion of each of said first sensing electrode wire (45), said second sensing electrode wire (47), said thermocouple wire (51), and said reference electrode wire (49) are located in an interior (61) of said middle section (31) of said first alumina tube (25); and (B) a data collector system (60) (i.e. a data acquisition system) comprising a first voltmeter (62), a second voltmeter (64), and a thermometer (66), and wherein said first sensing electrode (35) is in communication with said first voltmeter (62) via a first sensing electrode wire (45), wherein said second sensing electrode (37) is in communication with said second voltmeter (64) via said second sensing electrode wire (47), wherein said reference electrode (39) is in communication with said first voltmeter (62) and said second voltmeter (64) via a reference electrode wire (49), and wherein a thermocouple wire (51) is in communication with said thermocouple (32) and said thermometer (66), and wherein a portion of each of said first sensing electrode wire (45), said second sensing electrode wire (47), and said thermocouple wire (51) are located in an interior (61) of said middle section (31) of said first alumina tube (25).

In another embodiment of this invention incudes a method of measuring carbon monoxide in a combustion process environment comprising using a high temperature carbon monoxide sensor system comprising a high temperature carbon monoxide sensor (1) comprising a yttrium-stabilized zirconia interface based emf-measuring electrochemical sensor (41) and a nickel oxide (NiO) first sensing electrode (35) for targeting carbon monoxide gas at a temperature range from between about 1000 degrees Centigrade to about 1200 degrees Centigrade. In certain embodiments of this method, the combustion process environment is that of a power plant. In certain other embodiments of this invention, the method of measuring carbon monoxide includes wherein the high temperature carbon monoxide sensor (1) includes a platinum second sensing electrode (37) for targeting oxygen gas.

In another embodiment of this invention, a method of measuring carbon monoxide in a power plant environment is provided, the method comprising using a high temperature carbon monoxide sensor system comprising: (A) high temperature carbon monoxide sensor (1) comprises: (i) a housing (3) having a first end (5) and a second end (7) and a middle section (9) disposed between said first end (5) of said housing (3) and said second end (7) of said housing (3), said housing (3) having an external wall (11) and an internal wall (13); (ii) a chamber (15) having an internal wall (17) and an external wall (19), and wherein said chamber (15) having a first open end (21) and a second open end (23) and wherein the second open end (23) of said chamber (15) is opposite to said first open end (21) of said chamber (15), and wherein said external wall (19) of said chamber (15) is surrounded at least in part by said internal wall (13) of said housing (3); (iii) a first alumina tube (25) having an external wall (26) and an internal wall (27), said first alumina tube (25) has a first open end (28) and a second open end (29), and a middle section (31) disposed between said first open end (28) and said second open end (29) of said first alumina tube (25), wherein at least a portion of said first alumina tube (25) is located within said chamber (15); (iv) a thermocouple (32) wherein at least a portion of said thermocouple (32) is located within said chamber (15); (v) a sensor probe (33) wherein said sensor probe is located within and is in sealed engagement with said second open end (29) of said first alumina tube (25) wherein said sensor probe (33) comprises a first sensing electrode (35) and a reference electrode (39), and a yttrium-stabilized zirconia interface ("YSZ") (41), and optionally a second sensing electrode (37), wherein said yttrium-stabilized zirconia interface (41) is disposed between (a) said first sensing electrode (35) and (b) said reference electrode (39), or optionally wherein said yttrium-stabilized zirconia interface (41) is disposed between (a) said first sensing electrode (35) and said second sensing electrode (37) and (b) said reference electrode (39); (v) a porous ceramic element (43) (for example but not limited to a refractory brick, a ceramic porous brick, or a porous ceramic layer), wherein said porous ceramic element (43) is located within said second open end (23) of said chamber (15); and (vi) wherein said first sensing electrode (35) is in communication with a first sensing electrode wire (45), wherein said second sensing electrode (37) is in communication with a second sensing electrode wire (47), wherein said reference electrode (39) is in communication with a reference electrode wire (49), and wherein a thermocouple wire (51) is in communication with said thermocouple (32), and wherein at least a portion of each of said first sensing electrode wire (45), said second sensing electrode wire (47), said thermocouple wire (51), and said reference electrode wire (49) are located in an interior (61) of said middle section (31) of said first alumina tube (25); and (B) a data collector system (60) (i.e. a data acquisition system) comprising a first voltmeter (62), a second voltmeter (64), and a thermometer (66), and wherein said first sensing electrode (35) is in communication with said first voltmeter (62) via a first sensing electrode wire (45), wherein said second sensing electrode (37) is in communication with said second voltmeter (64) via said second sensing electrode wire (47), wherein said reference electrode (39) is in communication with said first voltmeter (62) and said second voltmeter (64) via a reference electrode wire (49), and wherein a thermocouple wire (51) is in communication with said thermocouple (32) and said thermometer (66), and wherein a portion of each of said first sensing electrode wire (45), said second sensing electrode wire (47), and said thermocouple wire (51) are located in an interior (61) of said middle section (31) of said first alumina tube (25).

An in-situ, accurate and robust sensor that can sustain high temperature of above 1000° C. is urgently needed for on-site combustion monitoring because it can give real-time and local data to control system to adjust the overall combustion efficiency. In this invention, we provide that nickel oxide (NiO) is a sensing material to CO which is a direct indicator of the status of combustion process of a power plant. Under the conditions of 0.5%-3% $O_2$ and 1000° C., the fabricated yttrium-stabilized zirconia (YSZ)-based mixed potential sensor using porous NiO demonstrates good sensitivity to CO, showing a signal as high as 36 mV to 1000 ppm CO. The effects of gas transport, structure and geometry of a NiO sensing electrode on sensing is provided herein. Results show that a fast gas transport is much beneficial to improved sensitivity. NiO of porous structure is much more sensitive to CO than that of dense structure. But $t_{90}$ (time to achieve 90% final signal magnitude) of the former is much longer due to slow gas diffusion inside the pores. It's worth noting that NiO sensor exhibits a positive relationship with CO content, opposite to other reported results of mixed potential sensors to CO. We find that it is due to the electrochemical reduction, instead of oxidation of CO during the interaction with NiO at 1000° C. Selectivity tests on how $CO_2$, $CH_4$ and steam affect CO sensing are also demonstrated. NiO is insensitive to even 10% $CO_2$. $CH_4$ does not shift the average value of CO sensing response. However, it makes the sensing signal fluctuate more intensively. 2% steam exerts a great influence on NiO's sensitivity to CO: it magnifies the sensitivity of porous NiO electrode to low CO range of 0-100 ppm, but inhibits that of 100 ppm to 1000 ppm.

With the global demand of energy expected to grow due to the population growth and progressive industrialization and the amount of renewable energy not being adequate,[1] fossil fuel (coal, oil and natural gas) would continue to dominate the global energy landscape for the foreseeable future.[2,3] Thus, with the fast-growing environmental and economic pressures as the world is shifting towards a low-carbon energy transition,[4] fossil fuel-based combustion processes, especially the electricity/heat generation that accounts for a large portion of total $CO_2$ emission,[5] should perform with higher efficiency and minimum emission. Among various strategies including equipment refurbishment and good maintenance practice,[6] upgrading combustion control system is an effective one, because it can directly improve the combustion efficiency by monitoring and adjusting the firing process.[7] It was reported that at Calaveras Power, JK Spruce Station, the heat rate and boiler efficiency was improved by 1.08% and 0.93%, respectively, after using a smart optimization technology.[8] However, the current combustion control is relatively far from satisfactory, especially for that in large-scale boilers in industry, such as boilers in coal-fired power plants. It is because in addition to depending on data analytics and process control algorithm, advanced combustion control system heavily relies on the quality of the actuator and sensor network. However, there is still a lack of well-functioning in-situ sensors for working conditions that are extremely aggressive.[9] An ideal scenario for in-situ sensors is that they can work in the temperature range of 1000-1500° C. and they are deployed across the whole boiler, since the combustion process is not uniform among local areas. If the local variations of combustion can be monitored in real time, the specific burners can be adjusted to respond to local deficient combustions. At the meantime, good sensitivity, durability and fast response time are expected, in spite of the presence of poisoning ashes, dusts and gases. Cost-effectiveness is also a consideration if successful, numerous sensors would be used for the power plant fleet all over the world.

Currently, continuous emissions monitoring systems (CEMS) using pollutant analyzer, algebra conversion equations or computer program to evaluate the gas or particulate specifies offers strong benefits to the power plant operation.[10] But they are expensive and require 1) the extraction of flue gas from the boiler, 2) the use of gas electrolytes. Even higher temperatures are possible with other oxygen ion conductors such as doped $ThO_2$. However, most YSZ-based mixed potential-type sensors reported are not suitable for the in-situ sensing in utility boilers because they consist of metallic sensing electrodes.[18] At high temperatures, very similar catalytic filters or traps, and 3) trained personnel to correctly handle the monitoring, which add a delay between the measurement and the real-time dynamic combustion.[11] Calorimetric analyzers using resistivity temperature detectors to detect the heat of oxidation from a catalyst layer have only been demonstrated as an extractive approach, which is not especially suitable for real-time boiler control.[9] Optical sensing approaches, e.g. tunable diode or quantum cascade laser spectroscopies are still not reliable enough given that a large amount of substances impede light transmission and the measured value is not local but an average one among the light path.[12] Chemical resistive sensors based on semiconducting oxides are used widely for various gas sensing at relatively lower temperature (<300° C.).[13-17] However, the lack of selectivity to some combustible gases and insufficient long-term stability at extremely high temperature may be the problem.

Fossil fuel sources are amenable to the use of high-temperature, oxygen ion-conducting solid electrolytes such as yttrium-stabilized or calcium-stabilized zirconium oxide (YSZ or CSZ) mixed potential sensors to enable closed-loop combustion control. The operating temperature up to 1400° C. can be undertaken by these solid kinetics on different metallic electrodes makes it difficult to establish an obvious mixed potential response.[19] There are few reports on the development of mixed potential-type YSZ-based sensor at temperatures higher than 900° C. to monitor combustion process.

At present, the combustion process monitoring is mostly accomplished by monitoring oxygen alone. However, a more accurate approach would be the concurrent measurement of the CO and oxygen concentration. The optimum condition for boilers in a coal-fired power plant is to operate in around 1-2% $O_2$ and 100-200 ppm CO depending on fuel type, which is near the stoichiometric point with the highest efficiency in safe operation.[9] In this work, we investigated NiO as the sensing material toward hundreds of ppm CO under the conditions of 0.5%-3% $O_2$ at 1000° C. The effects of flowrate of sample gas, geometry and structure of NiO electrode on the response magnitude and time were systematically studied. A one-of-a-kind YSZ-based mixed potential sensor with NiO sensing electrode was achieved, showing a response as high as 36 mV to 1000 ppm CO at 1000° C.

Sensor Fabrication

The mixed potential-type sensor structure is shown in FIG. 1(a), which consists of an 8YSZ electrolyte, a NiO and a porous Pt electrode in the sensing side, and another Pt electrode at the reference side. A dense circle YSZ pellet with a diameter of 2.5 cm and thickness of 0.2 cm was fabricated at first by mechanical pressing of YSZ powder (Tosoh-zirconia TZ-8YSB) followed by 1400° C. sintering at air for 4 h (hour). Then each circular electrode was made one by one by screen-printing the electrode material slurries onto the electrolyte followed by 1400° C. annealing in air for 4 h. NiO slurry was made by mixing the commercial NiO powders (Fuelcellmaterials NiO—F) and an organic vehicle. Pt slurry was supplied by ESL ElectroScience Inc. The RefPt (Pt electrode in the reference side) electrode was 1.5 cm in diameter, while two sensing electrodes, NiO and SenPt (Pt electrode in the sensing side), were 0.5 cm in diameter. Two different morphologies of NiO electrode, dense and porous, were prepared. X-ray diffraction (XRD, PANalytical X'Pert Pro) of the as-prepared NiO electrode are shown in FIG. 1(b), confirming the crystalline structures of NiO and YSZ that show no reactivity between them. A scanning electron microscope (SEM Hitach S-4700) was used to characterize their micro-morphologies of each electrode. Brunauer, Emmett and Teller (BET) surface area analysis (Micromeritics, RSAP 2020 Plus) was conducted to determine the electrode surface area and porosity.

Sensor Packaging and Lab-Test Station

A two-compartment configuration for lab-test, as shown in FIG. 1(c), was made via using two identical silica tubes (Advalue Technology LLC) pressing against the sensor pellet. Mica O-rings were positioned between $SiO_2$ tubes and the sensor pellet to obtain a good sealing. The outside diameter of the silica tubes matched the diameter of the sensor pallet. In the sensing side, an $Al_2O_3$ tube was flowing the mixed gases that consist of 2000 ppm CO gas, $N_2$ and air, in which the gas components were controlled by adjusting its mass flow rate by digital mass controllers (Alicat). On the reference side, an $Al_2O_3$ tube was used to feed air. All gases were in high quality supplied by Matheson Gas Inc. A multi-channel Gamry electrochemical workstation was applied to simultaneously record the voltage signals, with the working electrodes connected to the NiO sensing electrode and the Pt sensing electrode on the sensing side, and the reference electrode connected to the Pt reference electrode on the reference/air side.

Gas-Sensing Properties Measurements

The response of the sensor was measured in the atmosphere of 0-1000 ppm CO and 0.5%-3% $O_2$ balanced by $N_2$ with a total 200 sccm (standard $cm^3$/min) flowrate at temperature of 1000° C. NiO and Pt potentials were recorded: NiO vs. RefPt ($V_{NiO}$) and SenPt vs. RefPt ($V_{SenPt}$). The magnitude of responsey ($\Delta V$) was defined as the potential differences between sample gases and the base gas. For example, the response of NiO to 100 ppm CO is $\Delta V_{NiO}$(100 ppm)=$V_{NiO}$(100 ppm)–$V_{NiO}$(0 ppm). $t_{90}$, 90% response time, was defined as the duration to reach 90% value of $\Delta V$ in gas composition shift. Selectivity tests were also conducted for $CO_2$, steam and $CH_4$.

Results and Discussion:

Morphologies of Sensor Electrodes

Figure 2:
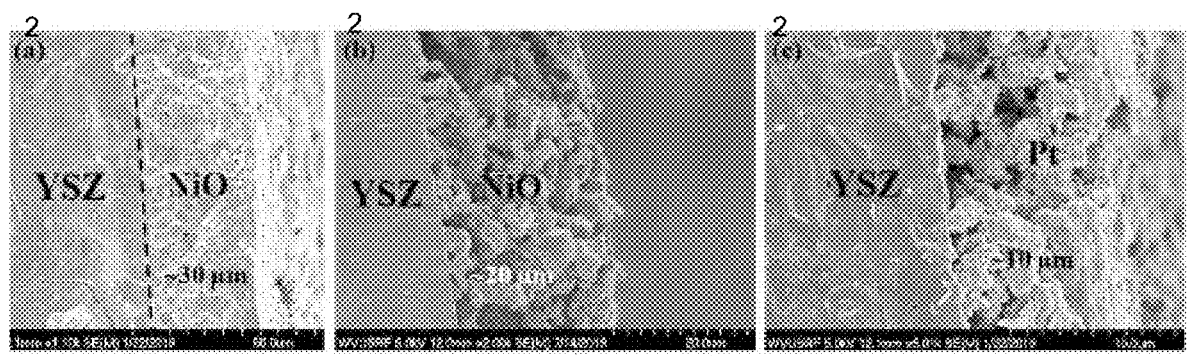
FIG. 2(a) shows SEM images of cross-sections of YSZ electrolyte and dense NiO electrode.
FIG. 2(b) shows SEM images of cross-sections of YSZ electrolyte and porous NiO electrode.
FIG. 2(c) shows SEM images of cross-sections of YSZ electrolyte and porous Pt electrode.

FIG. 2(a)-(c) show SEM photographs of the cross-sections of as-prepared dense NiO electrode/YSZ interface, porous NiO/YSZ interface and SenPt/YSZ interface, respectively, with the thickness of each electrode shown. It is seen from FIG. 2(a) that although some defects exist over the surface, the NiO film is quite dense. Therefore, we believe that most sensing signal of the dense NiO electrode comes from the TPB (three-phase boundary), which is the outer circle of the contact of dense NiO electrode, YSZ and sample gas. FIG. 2(c) is the morphology of a porous Pt electrode, representative of both SenPt and RefPt for they were made through the same process.

Figure 3:
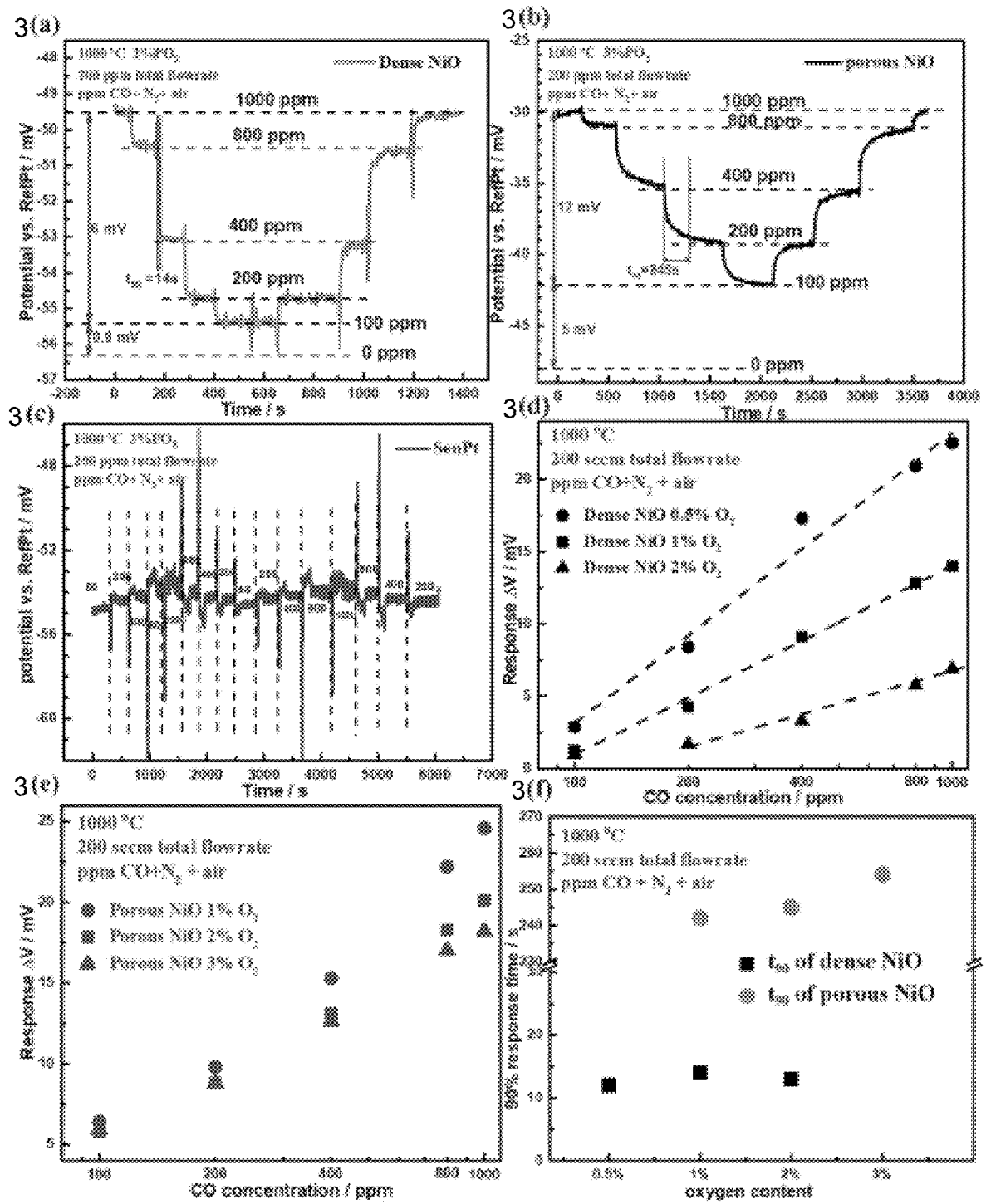
FIG. 3(a) shows sensing behavior to CO of dense NiO.
FIG. 3(b) shows sensing behavior to CO of porous NiO.
FIG. 3(c) shows sensing behavior to CO of SenPt, at atmospheres varying between 0-1000 ppm CO and 2%-3% $O_2$ at 900° C. and 1000° C. with the total flowrate of 200 sccm.
FIG. 3(d) shows the sensing response ($\Delta V$) to CO concentration for dense NiO.
FIG. 3(e) shows the sensing response ($\Delta V$) to CO concentration for porous NiO.
FIG. 3(f) shows the relationship of 90% response time $t_{90}$ with oxygen content for both dense and porous NiO.

CO sensing behavior of NiO electrodes Mixed potential on an electrode is established via at least two competing redox reactions occurring on the electrode, where due to zero net current and charge conservation, an electrochemically steady-state condition is achieved leading to a measurable mixed potential.[20, 21] FIG. 3 (a)-(c) show the typical sensing behaviors to CO for dense and porous NiO electrodes and SenPt electrode, in atmospheres varying between 0-1000 ppm CO and 0.5%-3% $O_2$ at 1000° C. with the total sample gas flowrate of 200 sccm. e SenPt does not show obvious sensitivity to CO and potentials are very close to the theoretical Nernst potential (Nernst: −53 mV for 3% $O_2$ at 1000° C.). It is primarily due to the fact that at temperature as high as 1000° C., the heterogeneous catalytic CO—$O_2$ reaction over metallic electrode surfaces is very fast, and very few CO reaches the TPB area. If some CO reaches TPB, the electrochemical activity of metallic electrode towards oxygen reduction reaction is so high that the mixed potential would not deviate much from its equilibrium oxygen potential. Both factors contribute to the low sensitivity to CO for the SenPt electrode at 1000° C.

In contrast, both dense NiO and porous NiO electrode exhibit obvious sensing ability to CO at 1000° C. and 0.5%-3% $O_2$, as seen in FIGS. 3(a), (b), (d) and (e). Although the porous NiO demonstrates superior sensitivity to CO as shown in FIG. 3(b), its response time ($t_{90}$=254 s) is not so good as that of the dense NiO ($t_{90}$=14 s). This is likely because the porous structure experienced a slow gas transport process, prolonging the transition time to the stable state. FIG. 3(f) demonstrates the relationship of $t_{90}$ with oxygen concentration for dense and porous NiO electrode. $T_{90}$ for porous NiO tends to increase with the increased oxygen content, while $t_{90}$ for dense NiO does not have a definite dependence on oxygen. For dense NiO, gas transport is not a limiting step given the 200 sccm flowrate, therefore $t_{90}$ reflects the electrochemical reaction kinetics. Since CO is at ppm level, the limiting step for electrochemical reactions should be related to CO rather than oxygen concentration, leading to the $T_{90}$ of dense NiO insensitive to oxygen concentration change. In contrast, for porous NiO electrode, higher oxygen concentration results in less CO reaching the sensing-active sites because the longer residence time leads to more thorough heterogeneous reaction between CO and $O_2$. This further slows the diffusion of CO due to the decreased CO concentration gradient. FIGS. 3(d) and (e) exhibit the relationship between sensing response ($\Delta V$) and CO concentration. For dense NiO, it basically shows the linear relationship of $\Delta V$s with the logarithm of CO, although in the case of 2% $O_2$, a good linearity is only seen for CO content ranging from 200 ppm to 1000 ppm. This supports the hypothesis that electrochemical reaction, instead of gas diffusion, is the rate-limiting step for the dense NiO electrode. In contrast, the non-linearity is relatively more dominant for the porous NiO electrode, which reveals that the gas diffusion plays a role in the sensing kinetics.

Figure 4:
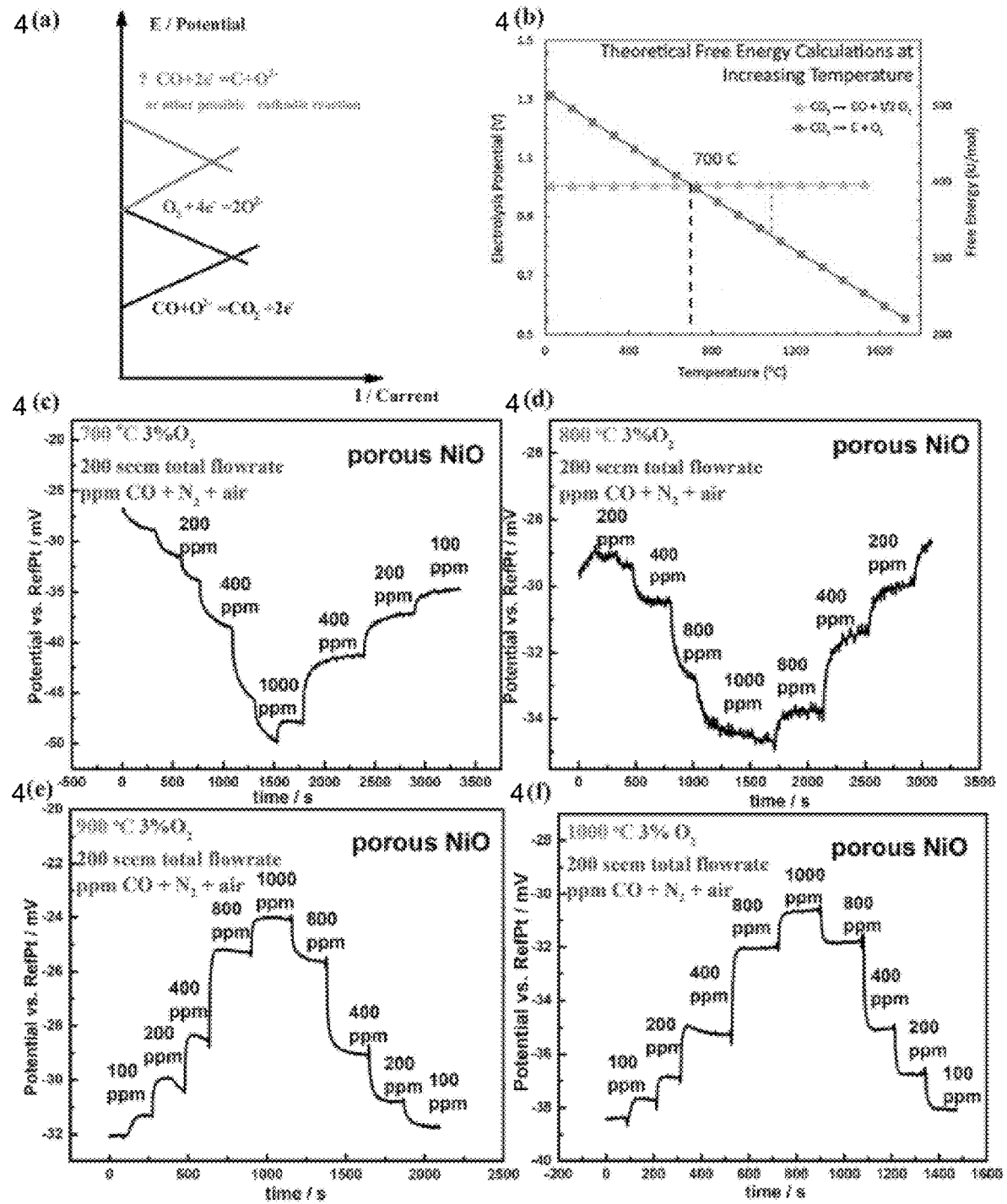
FIG. 4(a) shows (a) the schematics of the establishment of mixed potential of an electrode.
FIG. 4(b) shows theoretical calculation of free energy for $CO_2$ reduction to carbon and carbon monoxide.
FIG. 4(c) shows CO sensing testing for porous NiO in different temperature from 700° C. to 1000° C.
FIG. 4(d)) shows CO sensing testing for porous NiO in different temperature from 700° C. to 1000° C.
FIG. 4(e) shows CO sensing testing for porous NiO in different temperature from 700° C. to 1000° C.
FIG. 4(f) shows CO sensing testing for porous NiO in different temperature from 700° C. to 1000° C.

It is noteworthy that there is a positive relationship between the sensing response and CO concentration for NiO electrode as seen in FIGS. 3(d) and (e). This phenomenon is opposite to other published results in works of mixed potential-type CO sensor.[22-25] Mixed potential of an electrode is known to be established via electrochemical redox reactions occurring over the electrode. For scenarios that are commonly seen in literature, the mixed potential is formed due to CO oxidation and oxygen reduction, as illustrated by the black lines in FIG. 4(a). In this case, the mixed potential will go negatively with the increasing CO content. However, in this present work, we find that the measured mixed potential is increasing when the CO concentration goes up. Therefore, as shown by the red lines in FIG. 4(a), there should be a CO-involved reduction reaction occurred over the NiO surface, because only cathodic reactions can cause the mixed potential to increase. We think that the reduction of CO to carbon and oxygen ions is one possibility. FIG. 4(b) shows that the calculated Gibbs free energies for the formation of C and CO from $CO_2$ in standard condition defined in NIST-JANAF table.[26, 27] The standard $\Delta G$ of CO→C+½$O_2$ can be obtained by using the red line minus the green line. We can see that when the temperature is over 700° C., the Gibbs free energy of CO reduction to carbon and oxygen is negative, indicating that CO tends to decompose into carbon and oxygen. Of course, many factors have to be considered when we discuss thermodynamics, such as the partial pressure of each component and the involved possible reactions. To test this hypothesis of CO reduction, we measured the signal changes of the porous NiO electrode at different temperatures from 700° C. to 1000° C. with other conditions unchanged, as shown in FIG. 4(c)-(f). Below 900° C., the sensing behavior shows a negative correlation of the measured signal and CO concentration. However, when the temperature rises to 900° C. or higher, the opposite behavior occurs. This reversion at some extent supports our hypothesis that CO reduction may happen at higher temperatures and suggests that 900° C. may be the break-in point at which CO reduction starts to occur.

Figure 5:
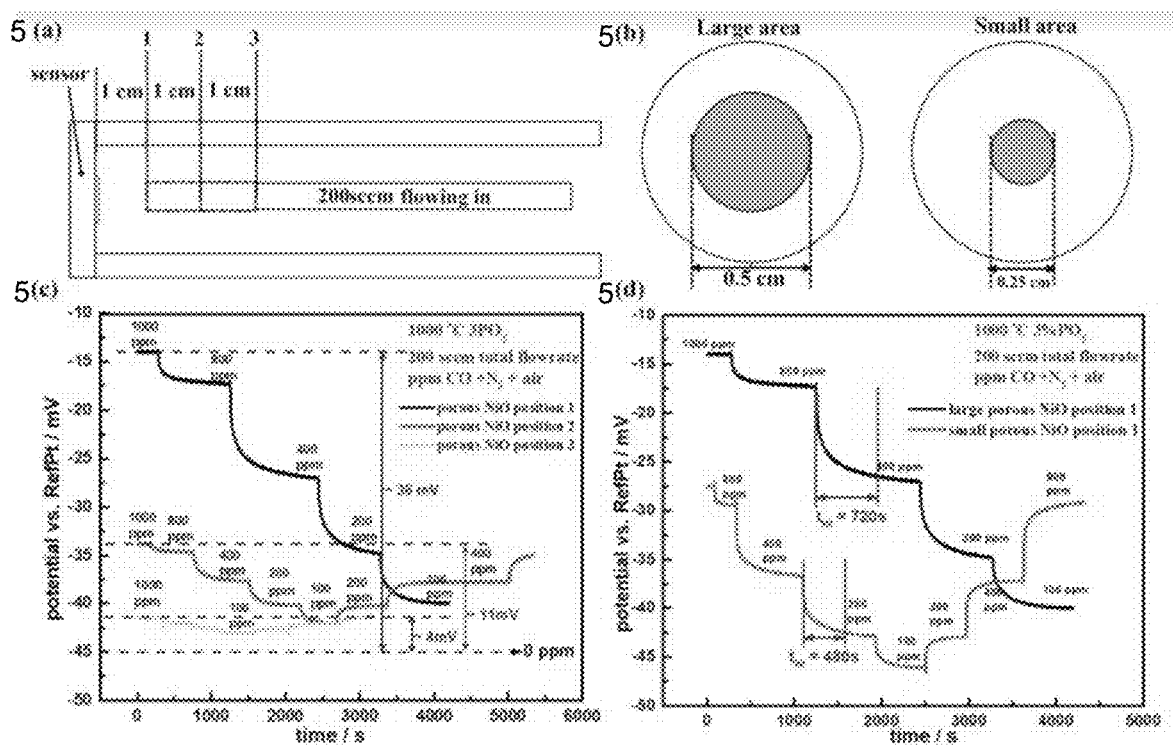
FIG. 5(a) shows the effect of gas transport on the CO sensing behavior of porous NiO at 3% $PO_2$ and 1000° C.
FIG. 5(b) shows the effect of electrode geometry on the sensing behavior.
FIG. 5(c) shows the effect of gas transport on the CO sensing behavior of porous NiO at 3% $PO_2$ and 1000° C. Top line=Porous NiO position 1; middle line=Porous NiO position 2; and lower line=Porous NiO position 3.
FIG. 5(d) shows the effect of electrode geometry on the sensing behavior. Top line=large porous NiO position 1; and bottom line=small porous NiO position 1.

FIGS. 5(a) and (c) demonstrate the effect of gas transport on the CO sensing behavior of porous NiO at 3% $P_{O2}$ and 1000° C. While the sample gas composition and total flowrate were kept unchanged, the gas transport was adjusted by changing the positions of the gas tube outlet as shown in FIG. 5(a). The highest sensitivity to CO is obtained for the case that the gas tube was placed in position 1, the nearest distance to sensor surface. It's not surprising to see such an influential effect of the CO transport to the sensitivity of porous NiO given the slow gas transport inside NiO pores can be a limiting factor. The response reached as high as 36 mV for 1000 ppm CO for the case of position 1, which suggests a strong interaction between CO and NiO given at 1000° C. oxygen reduction reactions are expected to be strong as well. FIGS. 5(b) and (d) reveal how the geometry of NiO electrode affects the sensing behavior. Large area porous NiO has better sensitivity but longer response time than the small area one. This result is understandable because more time is needed for the larger electrode to reach a stable state. However, for the relationship between electrode area and the sensitivity to CO, one shouldn't draw a conclusion of the larger the area, the higher the sensitivity, because sensitivity cannot be improved without limit just by enlarging electrode area. We believe this phenomenon has more to do with the 2D gas flow distribution relative to the electrode and the kinetics of CO reaction.

Selectivity Over Other Possible Combustion Gases

Figure 6:
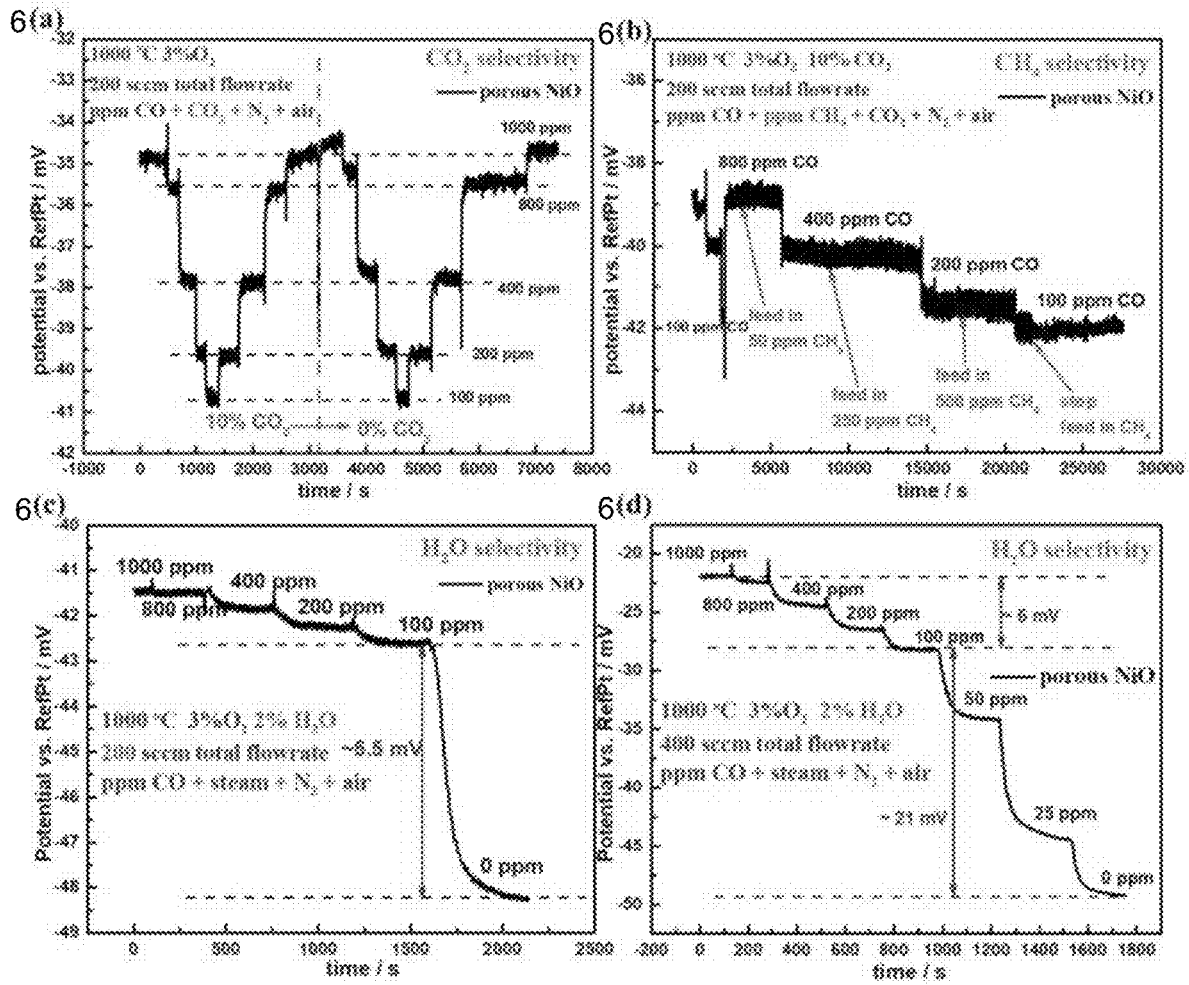
FIG. 6(a) shows CO sensing tests of porous NiO electrode at 1000° C. and 3% $O_2$ when including the effect of other gases 10% $CO_2$.
FIG. 6(b) shows CO sensing tests of porous NiO electrode at 1000° C. and 3% $O_2$ when including the effect of other gases ppm-scale $CH_4$.
FIG. 6(c) shows CO sensing tests of porous NiO electrode at 1000° C. and 3% $O_2$ when including the effect of other gases 2% $H_2O$ with 200 sccm total flowrate.
FIG. 6(d) shows CO sensing tests of porous NiO electrode at 1000° C. and 3% $O_2$ when including the effect of other gases and 2% $H_2O$ with 400 sccm total flowrate.
Figure 8:
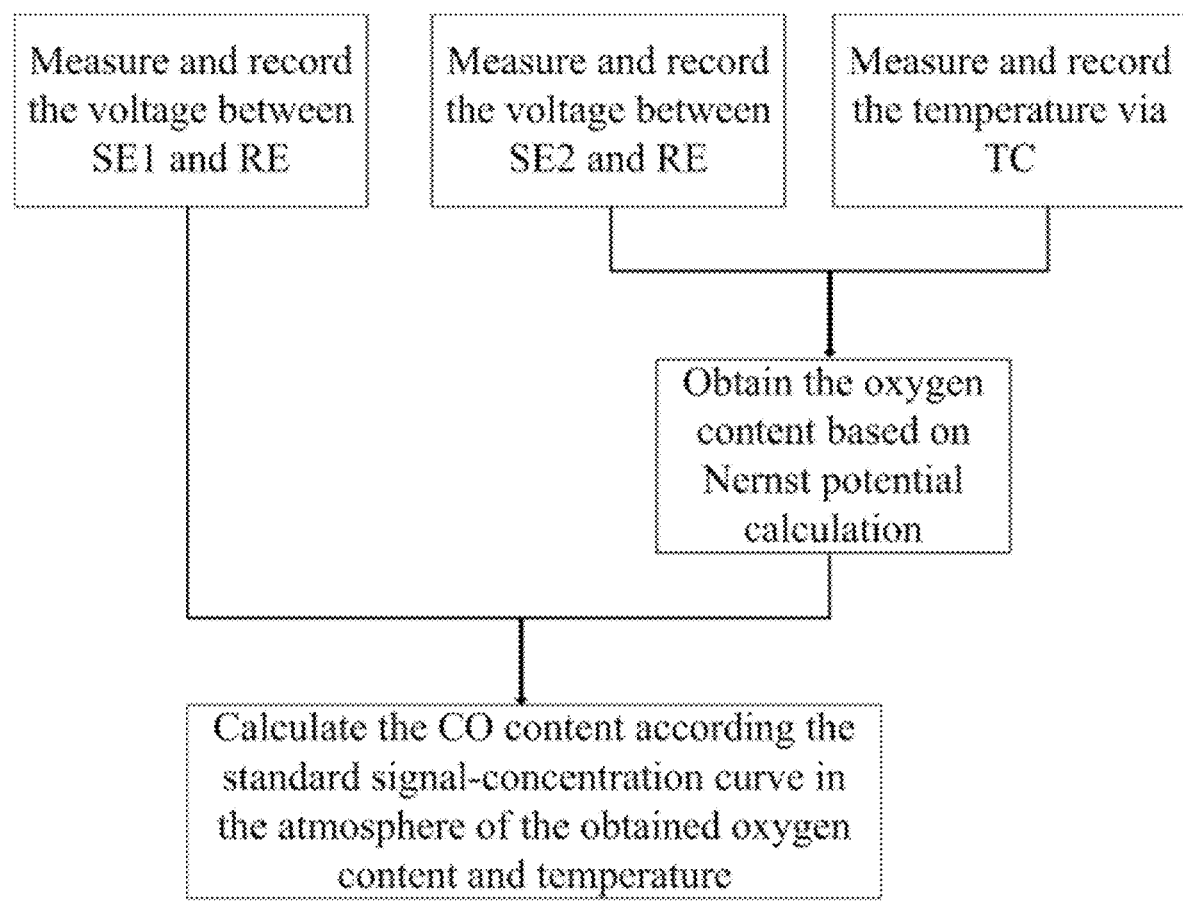
FIG. 8 shows a data acquisition process flow chart of the method of this invention.
Figure 9:
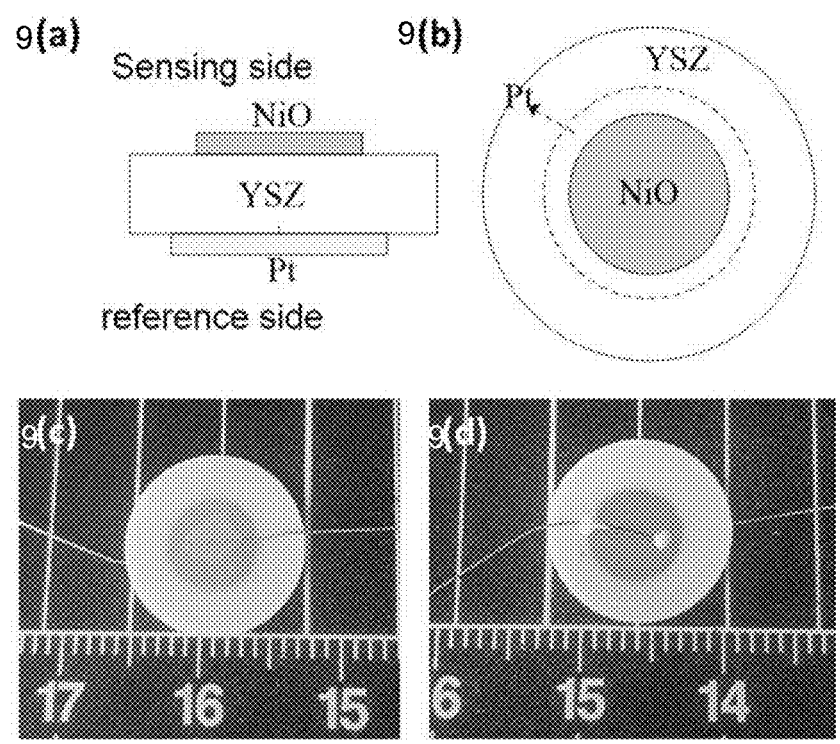
FIG. 9(a) shows a schematic of the sensor structure of this invention.
FIG. 9(b) shows a schematic of the sensor structure of this invention.
FIG. 9(c) shows an image of the sensor structure of this invention.
FIG. 9(d) shows an image of the sensor structure of this invention.
Figure 10:
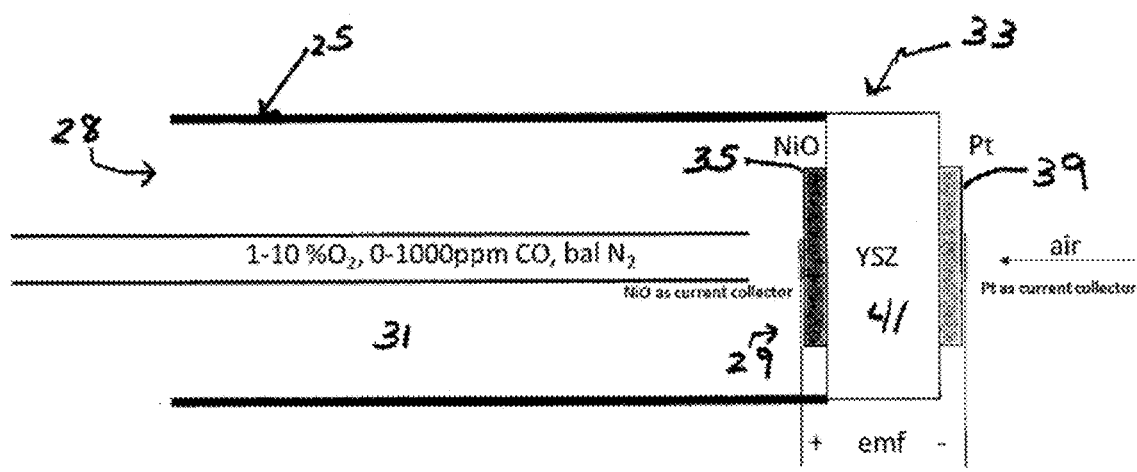
FIG. 10 shows a lab test configuration for the CO sensing testing for all lab-test results presented herein.
Figures 11A, 11B, 11C, 11D, 11E, 11F, 11G, 11H:
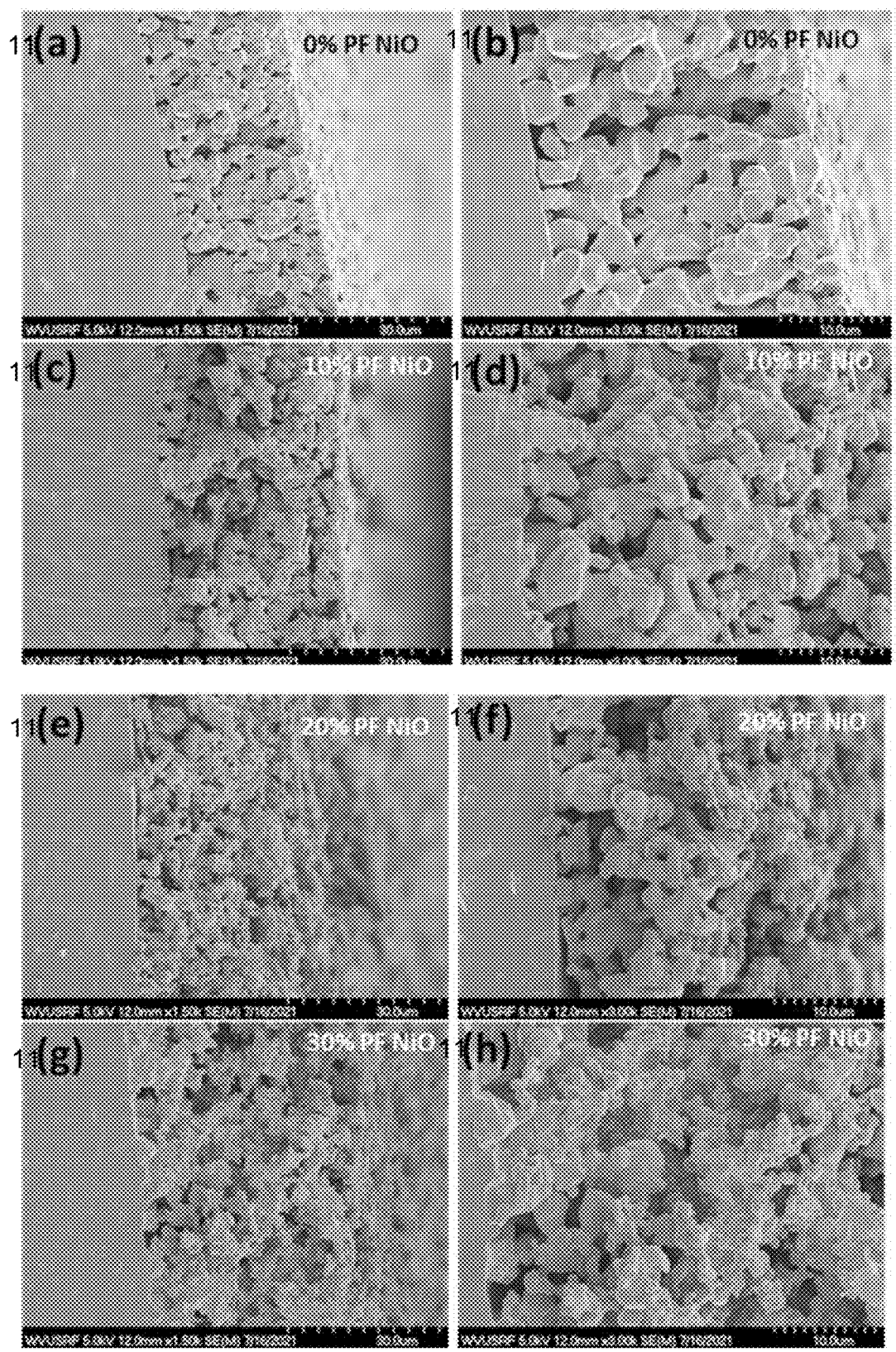
FIG. 11(a) shows SEM images of NiO sensing electrodes from different slurries of different pore former contents: 0% PF NiO=NiO electrode made by 0% added pore former NiO slurry. The sintering condition is 1400° C. for 4 h.
FIG. 11(b) shows SEM images of NiO sensing electrodes from different slurries of different pore former contents: 0% PF NiO=NiO electrode made by 0% added pore former NiO slurry. The sintering condition is 1400° C. for 4 h.
FIG. 11(c) shows SEM images of NiO sensing electrodes from different slurries of different pore former contents: 10% PF NiO=NiO electrode made by 10% added pore former NiO slurry. The sintering condition is 1400° C. for 4 h.
FIG. 11(d) shows SEM images of NiO sensing electrodes from different slurries of different pore former contents: 10% PF NiO=NiO electrode made by 10% added pore former NiO slurry. The sintering condition is 1400° C. for 4 h.
FIG. 11(e) shows SEM images of NiO sensing electrodes from different slurries of different pore former contents: 20% PF NiO=NiO electrode made by 20% added pore former NiO slurry. The sintering condition is 1400° C. for 4 h.
FIG. 11(f) shows SEM images of NiO sensing electrodes from different slurries of different pore former contents: 20% PF NiO=NiO electrode made by 20% added pore former NiO slurry. The sintering condition is 1400° C. for 4 h.
FIG. 11(g) shows SEM images of NiO sensing electrodes from different slurries of different pore former contents: 30% PF NiO=NiO electrode made by 30% added pore former NiO slurry. The sintering condition is 1400° C. for 4 h.
FIG. 11(h) shows SEM images of NiO sensing electrodes from different slurries of different pore former contents: 30% PF NiO=NiO electrode made by 30% added pore former NiO slurry. The sintering condition is 1400° C. for 4 h.
Figure 12A:
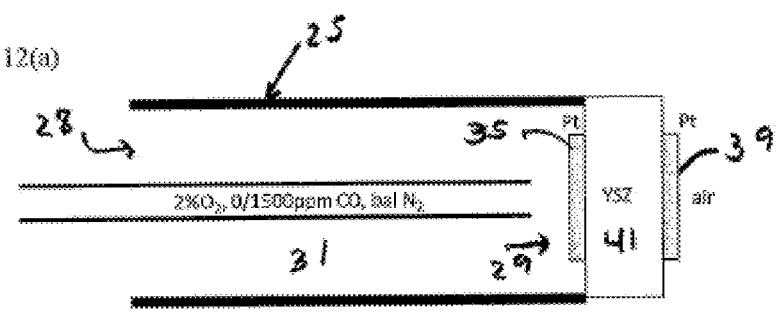
FIG. 12(a) shows platinum as the first sensing electrode to verify the temperatures of the furnace.
Figure 12B:
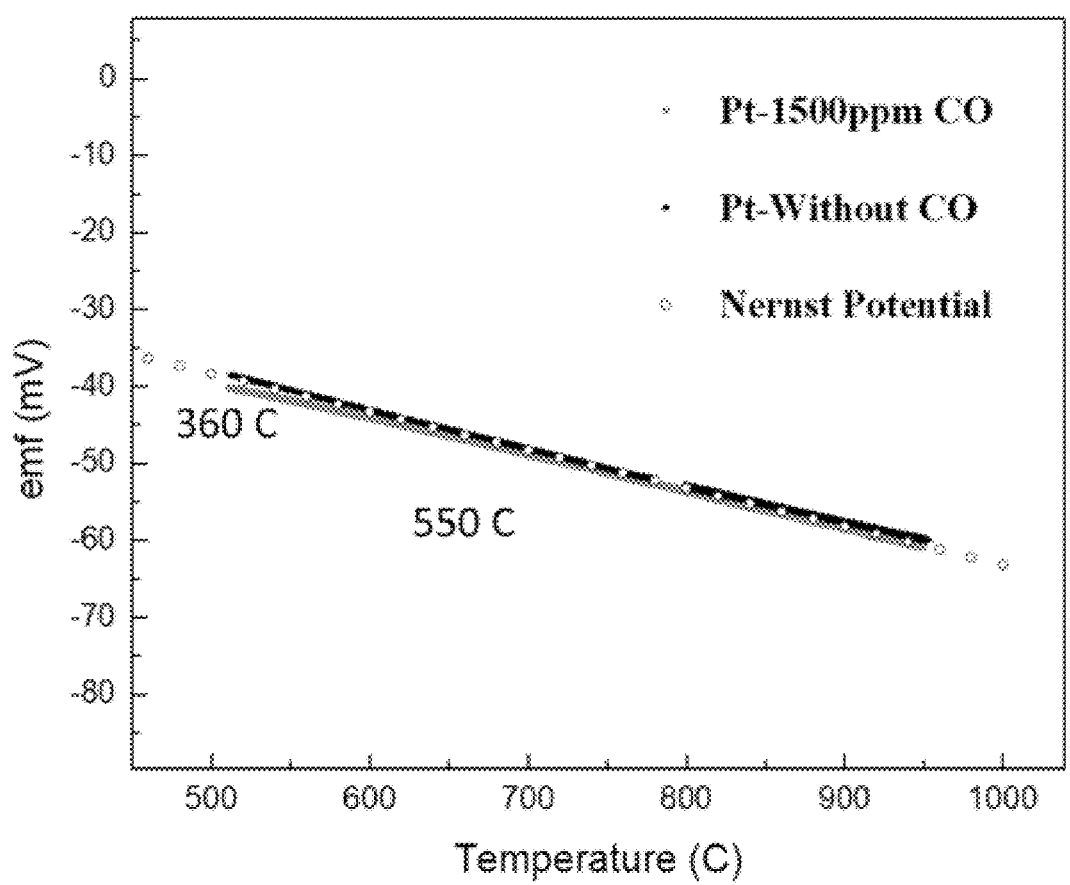
FIG. 12(b) shows a graph that the furnace temperature is accurate.
Figure 17A:
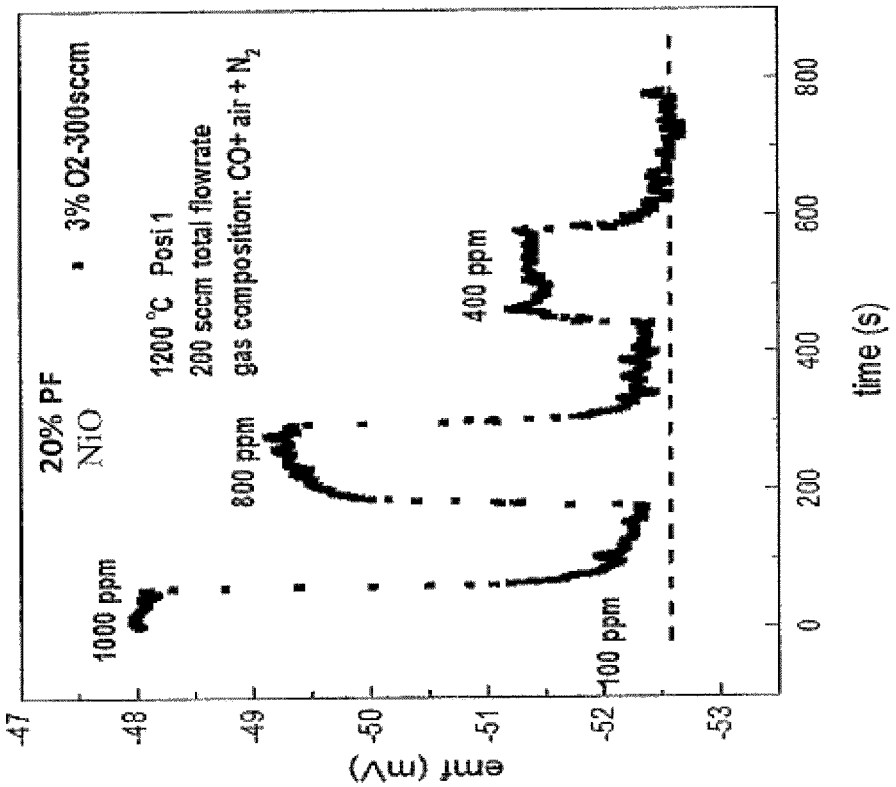
FIG. 17(a) shows sensing behavior of NiO to CO under 3% $O_2$ and 1200° C. vs. different flow rate.
Figure 17B:
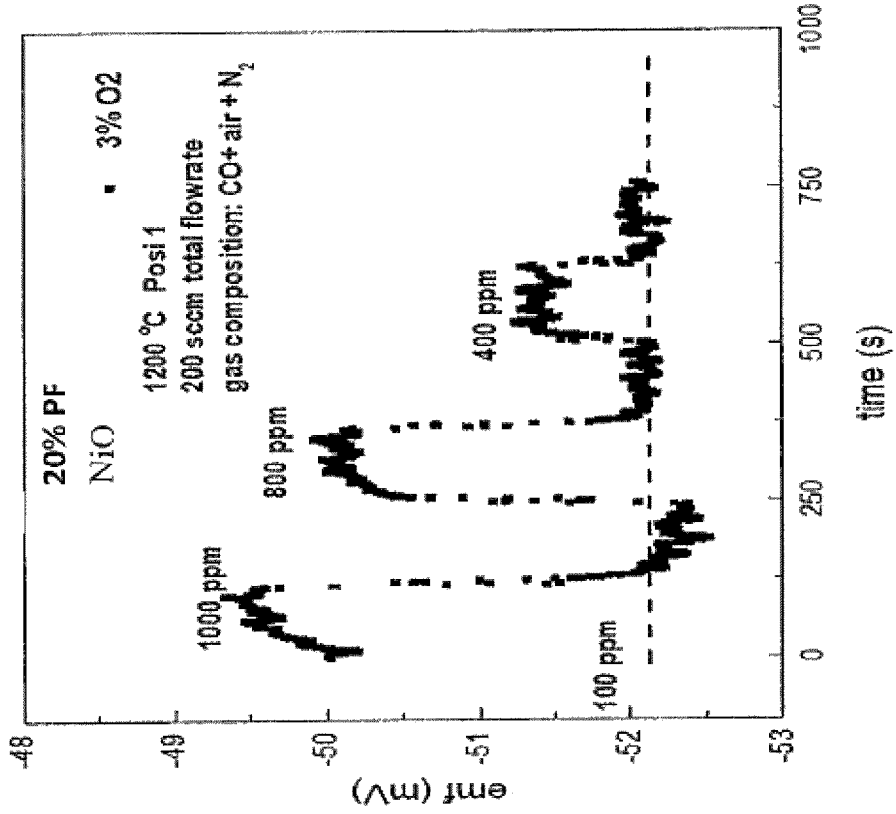
FIG. 17(b) shows sensing behavior of NiO to CO under 3% $O_2$ and 1200° C. vs. different flow rate.

Selectivity to CO over other major gas components in the utility boiler, such as $CO_2$, steam and hydrocarbons, is important. The effect of $CO_2$ on the sensing performance of CO is shown in FIG. 6(a). The red dash line indicates a change from 10% $CO_2$ to 0% $CO_2$. 10% $CO_2$ barely has any effect on the response, which means a very low selectivity of porous NiO electrode to $CO_2$. This result reveals that either the absorption of $CO_2$ is fairly low or $CO_2$ doesn't participate in the electrochemical reactions to build mixed potential, which is coincident with our speculation that CO is reduced to C and $O^{2-}$ instead of oxidized to $CO_2$ on NiO. The effect of $CH_4$ on the sensing performance of CO is shown in FIG. 6(b). It is seen that $CH_4$ in the atmosphere increases the signal fluctuation. However, $CH_4$ doesn't change the average sensing response to CO. Furthermore, after shutting off $CH_4$, the fluctuation starts to fade out which means the effect of $CH_4$ on the CO sensing is reversible.

The effect of $H_2O$ on the sensing performance of CO is shown in FIGS. 6(c) and (d). The only difference between FIGS. 6(c) and (d) is the total sample gas flowrate. In FIG. 6(c), the sensitivity to CO was greatly reduced due to the existence of 2% steam. The total flowrate was increased to improve the sensitivity according to the results shown above about the beneficial effect of flowrate. It is seen in FIG. 6(d) that above 100 ppm CO, the sensitivity is relatively low. In contrast, the NiO electrode shows greatly improved sensitivity to the low CO content range (0-100 ppm) compared to atmosphere without steam in FIG. 3 (a) and (b). One possibility is that the coverage of $H_2O$-related absorbates is high, leading to an easily saturated CO absorption, thus making the electrode less sensitive to higher CO contents.

Those persons of ordinary skill in the art understand that this invention provides that NiO is a promising material for in-situ high temperature CO sensing in utility boilers, such as coal-fired power plants. Its characteristics of enduring temperature as high as 1000° C. and good sensitivity, selectivity and response time to CO made it an excellent candidate for combustion monitoring sensor integrated into smart control system. Under the conditions of 0.5%-3% $O_2$ and 1000° C., the fabricated YSZ-based mixed potential sensor using porous NiO showed good sensitivity to ppm-scale CO. It showed a signal as high as 36 mV to 1000 ppm CO. In addition, how the sample gas transport and NiO electrode's structure and geometry affect the sensing behavior is provided. Results showed that sensitivity could be improved by facilitating gas diffusion. Porous NiO had higher sensitivity to CO than dense NiO. But in the meantime, the porous structure resulted in much longer response time. Selectivity tests on the effects of $CO_2$, $CH_4$ and steam on CO sensing were also conducted. NiO was insensitive to even 10% $CO_2$. $CH_4$ has not shifted the average value of CO sensing response. However, it made the sensing process unstable due to the enlarged signal fluctuation. 2% Steam exerted a great influence on NiO's sensing: porous NiO electrode showed no obvious variations with the CO content changing from 100 ppm to 1000 ppm; in contrast, the sensitivity of porous NiO electrode to low CO range of 0-100 ppm was enhanced significantly. This may be due to the decreased number of available adsorption sites for CO, which is preferably occupied by $H_2O$-related species, making the CO-related absorbates easily saturated when CO content is higher than 100 ppm. The potential of NiO exhibited a positive relationship with CO content. This is opposite to nearly all reported results in the works of mixed potential sensors to CO. While not being bound to any specific theory, we believe that it might be due to the electrochemical reduction of CO during the interaction with NiO at 1000° C. rather than being oxidized.

REFERENCES

1. Z. R. Chong, S. H. B. Yang, P. Babu, P. Linga and X.-S. Li, *Applied Energy,* 2016, 162, 1633-1652.
2. M. Ball and M. Wietschel, *International Journal of Hydrogen Energy,* 2009, 34, 615-627.
3. R. F. Aguilera and R. Aguilera, *Mineral Economics,* 2019, DOI: 10.1007/s13563-019-00192-5.
4. G. Wood, in *The Palgrave Handbook of Managing Fossil Fuels and Energy Transitions,* Springer, 2020, pp. 3-23.
5. IEA, *CO2 Emissions from Fuel Combustion* 2019, IEA, Paris, 2009.
6. R. J. Campbell, *Journal,* 2013.
7. N. Docquier and S. Candel, *Progress in Energy and Combustion Science,* 2002, 28, 107-150.
8. J. Sutton and P. Spinney, 2016.
9. P. Shuk and C. McGuire, *Sensors & Transducers,* 2017, 217, 1-13.
10. F. Liu, B. N. Duncan, N. A. Krotkov, L. N. Lamsal, S. Beirle, C. A. McLinden, D. Griffin, D. L. Goldberg and Z. Lu, *AGUFM,* 2019, 2019, A44E-07.
11. J. Kamas and J. Keeler, 1995.
12. P. Shuk, C. McGuire and E. Brosha, *Sensors & Transducers,* 2019, 229.

13. L.-S. Zhang, L.-Y. Jiang, C.-Q. Chen, W. Li, W.-G. Song and Y.-G. Guo, *Chemistry of Materials*, 2010, 22, 414-419.
14. W. Li, L.-S. Zhang, Q. Wang, Y. Yu, Z. Chen, C.-Y. Cao and W.-G. Song, *Journal of Materials Chemistry*, 2012, 22, 15342-15347.
15. Y. Lu, W. Li, J. Zhang, Y. Liu, P. Casey, S. Bateman, S. Z. Shen, J. Zhou, G. S. Zakharova and W. Chen, *Ferroelectrics*, 2015, 477, 93-102.
16. R. Purbia, Y. M. Kwon, H.-D. Kim, Y. S. Lee, H. Shin and J. M. Baik, *Journal of Materials Chemistry A*, 2020, 8, 11734-11742.
17. D. Wang, Y. Yin, P. Xu, F. Wang, P. Wang, J. Xu, X. Wang and X. Li, *Journal of Materials Chemistry A*, 2020, 8, 11188-11194.
18. X. Zhang, H. Kohler, M. Schwotzer, Y. Wu and U. Guth, *Sensors and Actuators B: Chemical*, 2019, 278, 117-125.
19. H. Okamoto, H. Obayashi and T. Kudo, *Solid State Ionics*, 1980, 1, 319-326.
20. T. Ritter, J. Lattus, G. Hagen and R. Moos, *Sensors and Actuators B: Chemical*, 2019, 287, 476-485.
21. N. Miura, T. Sato, S. A. Anggraini, H. Ikeda and S. Zhuiykov, *Ionics*, 2014, 20, 901-925.
22. S. A. Anggraini, Y. Fujio, H. Ikeda and N. Miura, *Analytica Chimica Acta*, 2017, 982, 176-184.
23. K. Mahendraprabhu, A. Selva Sharma and P. Elumalai, *Sensors and Actuators B: Chemical*, 2019, 283, 842-847.
24. N. D. Tho, D. V. Huong, H. T. Giang, P. Q. Ngan, G. H. Thai, D. T. A. Thu, D. T. Thu, N. T. M. Tuoi, N. N. Toan, P. D. Thang and H. N. Nhat, *Electrochimica Acta*, 2016, 190, 215-220.
25. M. Yamaguchi, S. A. Anggraini, Y. Fujio, M. Breedon, V. V. Plashnitsa and N. Miura, *Electrochimica Acta*, 2012, 76, 152-158.
26. J. Lau, G. Dey and S. Licht, *Energy Conversion and Management*, 2016, 122, 400-410.
27. M. W. Chase Jr, *J. Phys. Chem. Ref Data, Monograph*, 1998, 9.

It will be appreciated by those persons skilled in the art that changes could be made to embodiments of the present invention described herein without departing from the broad inventive concept thereof. It is understood, therefore, that this invention is not limited by any particular embodiments disclosed, but is intended to cover the modifications that are within the spirit and scope of the invention, as defined by the appended claims.

What is claimed is:

1. A high temperature carbon monoxide sensor comprising:
   (i) a housing having a first end and a second end and a middle section disposed between said first end of said housing and said second end of said housing, said housing having an external wall and an internal wall;
   (ii) a chamber having an internal wall and an external wall, and wherein said chamber having a first open end and a second open end and wherein the second open end of said chamber is opposite to said first open end of said chamber, and wherein said external wall of said chamber is surrounded at least in part by said internal wall of said housing; (iii) a thermocouple wherein at least a portion of said thermocouple is located within said chamber: (iv) a yttrium-stabilized zirconia interface based emf-measuring electrochemical sensor within said chamber, (v) a sensor probe wherein said sensor probe comprises a first sensing electrode and a reference electrode; wherein the first sensing electrode is a nickel oxide (NiO) electrode for targeting carbon monoxide gas at a temperature range from between about 1000 degrees Centigrade to about 1200 degrees Centigrade.

2. The high temperature carbon monoxide sensor of claim 1 including a platinum second sensing electrode for targeting oxygen gas.

3. The high temperature carbon monoxide sensor of claim 1 wherein said yttrium-stabilized zirconia is in the form of a solid electrolyte.

4. A high temperature carbon monoxide sensor comprising:
   (i) a housing having a first end and a second end and a middle section disposed between said first end of said housing and said second end of said housing, said housing having an external wall and an internal wall;
   (ii) a chamber having an internal wall and an external wall, and wherein said chamber having a first open end and a second open end and wherein the second open end of said chamber is opposite to said first open end of said chamber, and wherein said external wall of said chamber is surrounded at least in part by said internal wall of said housing; (iii) a first alumina tube having an external wall and an internal wall, said first alumina tube has a first open end and a second open end, and a middle section disposed between said first open end and said second open end of said first alumina tube, wherein at least a portion of said first alumina tube is located within said chamber; (iv) a thermocouple wherein at least a portion of said thermocouple is located within said chamber; (v) a sensor probe wherein said sensor probe is located within and is in sealed engagement with said second open end of said first alumina tube wherein said sensor probe comprises a first sensing electrode and a reference electrode, and a yttrium-stabilized zirconia interface, and optionally a second sensing electrode, wherein said yttrium-stabilized zirconia interface is disposed between (a) said first sensing electrode and (b) said reference electrode, or optionally wherein said yttrium-stabilized zirconia interface is disposed between (a) said first sensing electrode and said second sensing electrode and (b) said reference electrode; (v) a porous ceramic element, wherein said porous ceramic element is located within said second open end of said chamber; and (vi) wherein said first sensing electrode is in communication with a first sensing electrode wire, wherein said second sensing electrode is in communication with a second sensing electrode wire, wherein said reference electrode is in communication with a reference electrode wire, and wherein a thermocouple wire is in communication with said thermocouple, and wherein at least a portion of each of said first sensing electrode wire, said second sensing electrode wire, said thermocouple wire, and said reference electrode wire are located in an interior of said middle section of said first alumina tube.

5. The high temperature carbon monoxide sensor of claim 4 that includes an insulating layer wherein the insulating layer is in juxtaposition to at least a portion of said internal wall of said housing and at least a portion of said external wall of said chamber.

6. The high temperature carbon monoxide sensor of claim 4 wherein each of said first sensing electrode wire, said second sensing electrode wire, said thermocouple wire, and said reference electrode wire are made of a heat-resistant material.

7. The high temperature carbon monoxide sensor of claim 4 wherein said yttrium-stabilized zirconia interface is in the form of a solid electrolyte.

8. The high temperature carbon monoxide sensor of claim 4 wherein said first sensing electrode is a nickel oxide sensing electrode.

9. The high temperature carbon monoxide sensor of claim 4 wherein said second sensing electrode is a platinum sensing electrode.

10. The high temperature carbon monoxide sensor of claim 4 wherein said reference electrode is a platinum reference electrode.

11. A high temperature carbon monoxide sensor system comprising:
a high temperature carbon monoxide sensor comprising (i) a housing having a first end and a second end and a middle section disposed between said first end of said housing and said second end of said housing, said housing having an external wall and an internal wall; (ii) a chamber having an internal wall and an external wall, and wherein said chamber having a first open end and a second open end and wherein the second open end of said chamber is opposite to said first open end of said chamber, and wherein said external wall of said chamber is surrounded at least in part by said internal wall of said housing; (iii) a first alumina tube having an external wall and an internal wall, said first alumina tube has a first open end and a second open end, and a middle section disposed between said first open end and said second open end of said first alumina tube, wherein at least a portion of said first alumina tube is located within said chamber; (iv) a thermocouple wherein at least a portion of said thermocouple is located within said chamber; (v) a sensor probe wherein said sensor probe is located within and is in sealed engagement with said second open end of said first alumina tube wherein said sensor probe comprises a first sensing electrode and a reference electrode, and a yttrium-stabilized zirconia interface, and optionally a second sensing electrode, wherein said yttrium-stabilized zirconia interface is disposed between (a) said first sensing electrode and (b) said reference electrode, or optionally wherein said yttrium-stabilized zirconia interface is disposed between (a) said first sensing electrode and said second sensing electrode and (b) said reference electrode; (v) a porous ceramic element, wherein said porous ceramic element is located within said second open end of said chamber; and (vi) wherein said first sensing electrode is in communication with a first sensing electrode wire, wherein said second sensing electrode is in communication with a second sensing electrode wire, wherein said reference electrode is in communication with a reference electrode wire, and wherein a thermocouple wire is in communication with said thermocouple, and wherein at least a portion of each of said first sensing electrode wire, said second sensing electrode wire, said thermocouple wire, and said reference electrode wire are located in an interior of said middle section of said first alumina tube; and
(B) a data collector system comprising a first voltmeter, a second voltmeter, and a thermometer, and wherein said first sensing electrode is in communication with said first voltmeter via a first sensing electrode wire, wherein said second sensing electrode is in communication with said second voltmeter via said second sensing electrode wire, wherein said reference electrode is in communication with said first voltmeter and said second voltmeter via a reference electrode wire, and wherein a thermocouple wire is in communication with said thermocouple and said thermometer, and wherein a portion of each of said first sensing electrode wire, said second sensing electrode wire, and said thermocouple wire are located in an interior of said middle section of said first alumina tube.

12. The high temperature carbon monoxide sensor system of claim 11 that includes an insulating layer wherein said insulating layer is in juxtaposition to at least a portion of said internal wall of said housing and at least a portion of said external wall of said chamber.

13. The high temperature carbon monoxide sensor system of claim 11 wherein each of said first sensing electrode wire, said second sensing electrode wire, said thermocouple wire, and said reference electrode wire are made of a heat-resistant material.

14. The high temperature carbon monoxide sensor system of claim 11 wherein said yttrium-stabilized zirconia interface is in the form of a solid electrolyte.

15. A method of measuring carbon monoxide in a combustion process environment comprising placing the high temperature carbon monoxide sensor according to claim 4 in communication with a combustion process environment and reading a result from each of the first sensing electrode and the reference electrode.

16. The method of measuring carbon monoxide of claim 15 wherein said combustion process environment is that of a power plant.

17. The method of measuring carbon monoxide of claim 15 wherein said high temperature carbon monoxide sensor includes a platinum second sensing electrode for targeting oxygen gas.

18. The method of measuring carbon monoxide of claim 15 wherein said yttrium-stabilized zirconia is in the form of a solid electrolyte.

19. A method of measuring carbon monoxide in a combustion process environment comprising using a high temperature carbon monoxide sensor system comprising
(A) a high temperature carbon monoxide sensor comprising (i) a housing having a first end and a second end and a middle section disposed between said first end of said housing and said second end of said housing, said housing having an external wall and an internal wall; (ii) a chamber having an internal wall and an external wall, and wherein said chamber having a first open end and a second open end and wherein the second open end of said chamber is opposite to said first open end of said chamber, and wherein said external wall of said chamber is surrounded at least in part by said internal wall of said housing; (iii) a first alumina tube having an external wall and an internal wall, said first alumina tube has a first open end and a second open end, and a middle section disposed between said first open end and said second open end of said first alumina tube, wherein at least a portion of said first alumina tube is located within said chamber; (iv) a thermocouple wherein at least a portion of said thermocouple is located within said chamber; (v) a sensor probe wherein said sensor probe is located within and is in sealed engagement with said second open end of said first alumina tube wherein said sensor probe comprises a first sensing electrode and a reference electrode, and a yttrium-stabilized zirconia interface, and optionally a second sensing electrode, wherein said yttrium-stabilized zirconia interface is disposed between (a) said first sensing electrode and (b) said reference electrode, or optionally wherein said yttrium-stabilized zirconia interface is disposed between (a) said first sensing electrode and said second sensing electrode and (b) said reference electrode; (v) a porous ceramic element, wherein said porous ceramic element is located within said second open end of said chamber; and (vi) wherein said first sensing electrode is in communication with a first sensing electrode wire, wherein said second sensing electrode is in communication with a second sensing electrode wire, wherein said reference electrode is in communication with a reference electrode wire, and wherein a thermocouple wire is in communication with said thermocouple, and wherein at least a portion of each of said first sensing electrode wire, said second sensing electrode wire, said thermocouple wire, and said reference electrode wire are located in an interior of said middle section of said first alumina tube; and (B) a data collector system comprising a first voltmeter, a second voltmeter, and a thermometer, and wherein said first sensing electrode is in communication with said first voltmeter via a first sensing electrode wire, wherein said second sensing electrode is in communication with said second voltmeter via said second sensing electrode wire, wherein said reference electrode is in communication with said first voltmeter and said second voltmeter via a reference electrode wire, and wherein a thermocouple wire is in communication with said thermocouple and said thermometer, and wherein a portion of each of said first sensing electrode wire, said second sensing electrode wire, and said thermocouple wire are located in an interior of said middle section of said first alumina tube.

20. The method of measuring carbon monoxide in a combustion process environment of claim 19 including wherein said first sensing electrode is a nickel oxide sensing electrode, said second sensing electrode is a platinum sensing electrode, and said reference electrode is a platinum reference electrode.

21. A high temperature carbon monoxide sensor comprising a yttrium-stabilized zirconia interface based emf-measuring electrochemical sensor, a first sensing electrode for targeting carbon monoxide gas at a temperature range from between about 1000 degrees Centigrade to about 1200 degrees Centigrade, and a second sensing electrode, wherein said first sensing electrode is made of a material that is one independently selected from the group consisting essentially of (i) NiO, (ii) NiO doped with the following doping material $ZrO_2$ and doping element stabilized zirconia such as Yttria stabilized Zirconia (YSZ), Samaria Stabilized Zirconia (SSZ), and Calcium stabilized Zirconia (CSZ), (iii) NiO doped with ceria, (iv) NiO doped with ceria that is one selected from the group consisting essentially of Gadolinium doped Ceria (GDC) and Samarium doped Ceria (SDC); (v) NiO doped with CuO, (vi) NiO doped with FeO, (vii) NiO doped with $Al_2O_3$, (viii) NiO doped with infiltrated spinel, (ix) NiO doped with NiFe spinel, (x) Ni doped with NiAl spinel, and (xi) NiO doped with platinum, and wherein said second sensing electrode is made of a material that is selected from the group consisting essentially of (i) NiO, (ii) NiO doped with the following doping material $ZrO_2$ and doping element stabilized zirconia such as Yttria stabilized Zirconia (YSZ), Samaria Stabilized Zirconia (SSZ), and Calcium stabilized Zirconia (CSZ), (iii) NiO doped with ceria, (iv) NiO doped with ceria that is one selected from the group consisting essentially of Gadolinium doped Ceria (GDC) and Samarium doped Ceria (SDC); (v) NiO doped with CuO, (vi) NiO doped with FeO, (vii) NiO doped with $Al_2O_3$, (viii) NiO doped with infiltrated spinel, (ix) NiO doped with NiFe spinel, (x) NiO doped with NiAl spinel, and (xi) NiO doped with platinum.

\* \* \* \* \*